United States Patent [19]

Mowbray et al.

[11] Patent Number: 5,863,917

[45] Date of Patent: Jan. 26, 1999

[54] QUINOXALINE DERIVATIVES USEFUL IN THERAPY

[75] Inventors: Charles Eric Mowbray; Alan Stobie, both of Sandwich, United Kingdom

[73] Assignee: Pfizer, Inc., New York, N.Y.

[21] Appl. No.: 938,230

[22] Filed: Sep. 26, 1997

[30] Foreign Application Priority Data

Mar. 1, 1996 [GB] United Kingdom .................. 9604400

[51] Int. Cl.⁶ ...................... A61K 31/495; C07D 241/52
[52] U.S. Cl. ............................................. 514/249; 544/354
[58] Field of Search ............................. 514/249; 544/354

[56] References Cited

U.S. PATENT DOCUMENTS 5,187,168  2/1993  Primeau et al. ......................... 514/259

FOREIGN PATENT DOCUMENTS

| 03220124 | 9/1991 | Japan . |
|---|---|---|
| WO9308188 | 4/1993 | WIPO . |
| WO9400124 | 1/1994 | WIPO . |
| WO9512417 | 5/1995 | WIPO . |
| WO9604288 | 2/1996 | WIPO . |
| WO9609295 | 3/1996 | WIPO . |

OTHER PUBLICATIONS

CA 127: 200049 Quinoxaline derivatives for treating tinnitus. Sands, Apr. 11, 1997.

*Primary Examiner*—Joseph K. McKane
*Attorney, Agent, or Firm*—Peter C. Richardson; Paul H. Ginsburg; Mark Dryer

[57] ABSTRACT

The invention provides compounds of formula I, wherein
$R^1$ and $R^2$ independently represent Cl or $C_{1-6}$ alkyl;
$R^3$ represents $XCO_2R^4$, $XCONHSO_2R^5$, $YNHSO_2R^5$ or $XR^6$;
$R^4$ represents H or $C_{1-6}$ alkyl (optionally substituted by aryl or heterocyclyl);
$R^5$ represents $CF_3$, heterocyclyl or $C_{1-6}$ alkyl (optionally substituted by aryl or heterocyclyl);
$R^6$ represents an acidic heterocycle;
X represents a $C_{1-6}$ alkyl diradical (optionally subsituted by aryl or heterocyclyl); and
Y represents a $C_{2-6}$ alkyl diradical (optionally substituted by aryl or heterocyclyl); provided that when $R^1$ and $R^2$ each represent Cl, then $R^3$ does not represent $CH_2CO_2H$, $CH_2CO_2CH_3$, $CH_2CH_2NHSO_2CF_3$ or 5-tetrazolylmethyl; and pharmaceutically acceptable salts thereof.

The compounds are indicated as anxiolytics, anticonvulsants, analgesics and neuroprotectives.

8 Claims, No Drawings

QUINOXALINE DERIVATIVES USEFUL IN THERAPY

This invention relates to quinoxaline derivatives useful in therapy.

L-Glutamic acid is an excitatory amino acid neurotransmitter whose physiological role in the brain involves interaction with four receptors, three of which are named after the selective agonists NMDA (N-methyl-D-aspartate), AMPA (2-amino-3-hydroxy-5-methyl4-isoxazolepropionic acid) and kainate. The fourth receptor is termed the metabotropic receptor. In addition to a binding site for glutamic acid, the NMDA receptor possesses high affinity binding sites for dissociative anaesthetics (e.g. ketamine), polyamines (e.g. spermine), glycine and certain metal ions (e.g. $Mg^{2+}$, $Zn^{2+}$). Since the NMDA receptor has an absolute requirement to bind glycine for activation to occur, glycine antagonists can act as functional NMDA antagonists.

In the region of a cerebral infarct, for example, anoxia causes abnormally high concentrations of glutamic acid to be released, which leads to an over-stimulation of NMDA receptors, resulting in the degeneration and death of neurones. Thus, NMDA receptor antagonists, which have been shown to block the neurotoxic effects of glutamic acid in vitro and in vivo, may be useful in the treatment and/or prevention of pathological conditions in which NMDA receptor activation is thought to be important. Examples of such conditions include neurodegenerative disorders including senile dementia and Alzheimer's disease and those arising from events such as stroke, transient ischaemic attack, peri-operative ischaemia and traumatic head injury to the brain or spinal cord. They may also have utility in conditions in which peripheral nerve function has been impaired such as retinal and macular degeneration.

Furthermore, NMDA antagonists have been shown to possess anti-convulsant and anxiolytic activity and may therefore be used to treat epilepsy and anxiety. They may also be useful in the treatment of pain.

NMDA antagonists may also attenuate the effects of alcohol withdrawal from physically dependent animals (K. A. Grant et al. J. Pharm. Exp. Ther. (1992), 260, 1017) and thus NMDA antagonists may be of use in the treatment of alcohol addiction.

Various derivatives of 1,2,3,4-tetrahydroquinoline-2,4-dione have been described as NMDA (glycine site) antagonists (see EP-A-0459561 and EP-A-0481676), while WO-A-91/13878 and JP-A-3220124 describe 1,4-dihydroquinoxalin-2,3-diones as glutamic acid antagonists. WO-A-94/00124 describes 1,4-dihydroquinoxalin-2,3-diones (including 6,7-dichloro-5-nitro-1,4-dihydroquinoxalin-2,3-dione) having high affinity for the glycine binding site with utility for treating stroke and related disorders.

International Patent Application N° PCT/EP95/03559 (published 28 Mar. 1996) discloses a number of quinoxalinsulphonamide derivatives which are indicated as anxiolytic, anticonvulsant, analgesic or neuroprotective agents.

According to the present invention, there is provided a compound of formula 1,

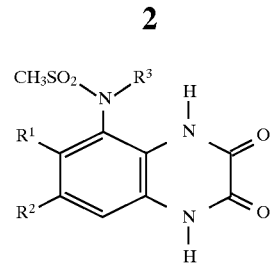

wherein
$R^1$ and $R^2$ independently represent Cl or $C_{1-6}$ alkyl;
$R^3$ represents $XCO_2R^4$, $XCONHSO_2R^5$, $YNHSO_2R^5$ or $XR^6$;
$R^4$ represents H or $C_{1-6}$ alkyl (optionally substituted by aryl or heterocyclyl);
$R^5$ represents $CF_3$, heterocyclyl or $C_{1-6}$ alkyl (optionally substituted by aryl or heterocyclyl);
$R^6$ represents an acidic heterocycle;
X represents a $C_{1-6}$ alkyl diradical (optionally substituted by aryl or heterocyclyl); and
Y represents a $C_{2-6}$ alkyl diradical (optionally substituted by aryl or heterocyclyl); provided that when $R^1$ and $R^2$ each represent Cl, then $R^3$ does not represent $CH_2CO_2H$, $CH_2CO_2CH_3$, $CH_2CH_2NHSO_2CF_3$ or 5-tetrazolylmethyl; and pharmaceutically acceptable salts thereof (referred to together herein as "the compounds of the inventions").

Pharmaceutically acceptable salts include salts of any acidic groups which may be present, for example alkali metal salts (such as sodium salts) of carboxylic acid groups. The dione group may also ionise and form salts with sodium, ethanolamine and diethanolamine, for example.

Alkyl groups represented by $R^1$, $R^2$, $R^4$ and $R^5$ may be straight, cyclic or branched chain.

Alkyl diradicals represented by X and Y may be straight, cyclic or branched chain. Examples of such groups include —$CH_2$—, —$CH_2CH_2$— and —$CH(CH_3)CH_2$—. Heterocyclic groups represented or comprised by $R^4$, $R^5$, X and Y include aromatic and non-aromatic groups containing 5 or 6 ring atoms, up to 3 of which may be selected from N, O or S. Specific heterocyclic groups are pyridinyl, imidazolyl, pyrimidinyl, pyrazolyl, triazolyl, pyrazinyl, tetrazolyl, furyl, thienyl, isoxazolyl and thiazolyl. Optionally, such groups may be substituted by methyl or halogen. In addition, they may be fused to a benzene ring. Therefore, $R^5$ may represent a methylimidazole group, for example.

"Aryl" means an aromatic hydrocarbon. Aryl groups comprised by $R^4$, $R^5$, X and Y may contain 6 or 10 carbon atoms, such as phenyl or naphthyl. Optionally, they may be substituted by methyl or halogen. In addition, they may be fused to a heterocyclic ring containing 5 or 6 ring atoms, up to 3 of which may be selected from N, O or S.

Acidic heterocycles that $R^6$ represents are those which, when a sample of them is exposed to physiological pH (7.4), more than 50% of the molecules are ionised. Examples include oxadiazolone and tetrazole. The heterocycles may be substituted by methyl or halogen, provided that the acidity criterion set out above is still satisfied.

"Halogen" means fluoro, chloro, bromo or iodo. Preferred groups are fluoro, chloro and bromo.

In some instances the compounds of the invention may exist as tautomers and all such tautomers are included within the scope of the invention, whether separated or not. In addition compounds containing asymmetric centres can exist as enantiomers and diastereoisomers, and the invention includes the separated individual isomers as well as mixtures of isomers. In particular, rotation about the bond between the sulphonamide nitrogen atom and the 1,4-dihydro-2,3- dioxoquinoxaline ring may be restricted, and so atropisomerism may arise. Optical isomers (including atropisomers) may be separated using conventional techniques such as fractional crystallization of diastereomeric derivatives.

Preferred groups of compounds which may be mentioned include those in which:

(a) $R^1$ represents Cl;
(b) $R^2$ represents methyl; and
(c) $R^3$ represents $CH_2CO_2H$, $CH(CH_3)CO_2H$, or $(CH_2)_3CO_2H$.

The invention further provides a process for the production of a compound of formula I, as defined above, or a pharmaceutically acceptable salt thereof, which comprises removing the protecting groups from a compound of formula II,

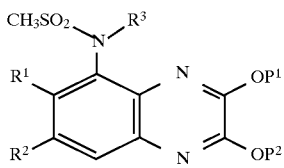

II wherein $R^{1-3}$ are as defined above and $P^1$ and $P^2$ are hydroxy protecting groups, and where desired or necessary converting the resulting compound into a pharmaceutically acceptable salt or vice versa.

Protecting groups which $P^1$ and $P^2$ may represent include benzyl and $C_{1-6}$ alkyl, in particular methyl. These protecting groups may be removed using conventional deprotection methods (see 'Protective Groups in Organic Synthesis' by T W Greene and P G M Wuts, John Wiley and Sons Inc, 1991). For example, when they represent methyl, they may be removed by acidic hydrolysis using dilute aqueous hydrochloric acid (e.g. 2 molar). The reaction is typically carried out by heating the compound of formula II, preferably under reflux, in a mixture of dilute aqueous hydrochloric acid and a suitable organic solvent such as dioxane or acetone for, say, 2 to 48 hours until reaction is complete. The compound of the invention can then be isolated and purified by conventional procedures.

Compounds of formula II, as defined above, form a further aspect of the invention.

When protecting groups $P^1$ and $P^2$ are removed in the above process, if $R^3$ represents $XCO_2R^4$ and $R^4$ represents $C_{1-6}$ alkyl (optionally substituted), this $R^4$ group may be replaced with H by the conditions of the reaction. A compound of formula I in which $R^4$ represents $C_{1-6}$ alkyl (optionally substituted) may be obtained by reaction of a corresponding compound of formula I in which $R^4$ represents H with the appropriate alcohol of formula $R^4OH$ using conventional methods.

Compounds of formula II in which $R^3$ represents $XCO_2R^4$ may be prepared by reaction of a compound of formula III,

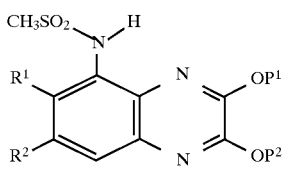

III in which $R^1$, $R^2$, $P^1$ and $P^2$ are as defined above, with a compound of formula Hal-$XCO_2R^4$, wherein Hal represents Cl, Br or I and X is as defined above. The reaction may be carried out in the presence of a base (such as potassium carbonate) in a suitable solvent (such as acetone) at an elevated temperature (such as the reflux temperature of the solvent).

In addition, compounds of formula II in which $R^3$ represents $XCO_2H$ may be prepared by reaction of a compound of formula III, as defined above, with a compound of formula Hal-$XCH_2OH$, wherein X and Hal are as defined above, to give a compound of formula II in which $R^3$ represents $XCH_2OH$, followed by oxidation using conventional methods, such as the action of pyridinium dichromate.

Compounds of formula II in which $R^3$ represents $YNHSO_2R^5$ may be prepared in three stages:

(a) Alkylation of a compound of formula III, as defined above, with a compound of formula Hal-Y-(N-phthalimide), wherein Hal represents Cl, Br or I. The reaction may be carried out in the presence of a base (such as potassium carbonate) in a suitable solvent (such as acetone) at an elevated temperature (such as the reflux temperature of the solvent).

(b) Deprotection of the alkylated compound to yield an $NH_2$ group. The reaction may be carried out using hydrazine hydrate in a suitable solvent (such as dichloromethane and methanol) at an elevated temperature (such as the reflux temperature of the solvent).

(c) Reaction of the amino compound with a compound of formula $(R^5SO_2)_2O$ or $R^5SO_2Cl$. The reaction may be carried out in a suitable solvent (such as dry tetrahydrofuran), at room temperature.

Compounds of formula II in which $R^3$ represents $XCONHSO_2R^5$ or $XR^6$ may be prepared from corresponding compounds of formula II in which $R^3$ represents $XCO_2R^4$ by conventional methods, as illustrated by the Examples.

Compounds of formula III can be prepared by sulphonylation of a corresponding quinoxaline of formula IV,

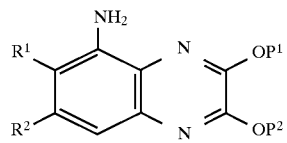

IV in which $R^1$, $R^2$, $P^1$ and $P^2$ are as defined above, using the appropriate sulphonyl chloride $CH_3SO_2Cl$ or anhydride $(CH_3SO_2)_2O$, in a suitable organic solvent, e.g. dichloromethane or tetrahydrofuran, in the presence of an acid acceptor such as pyridine or triethylamine. With some starting materials, if a large excess of the sulphonyl chloride or anhydride is used, then di-sulphonylation or some degree of di-sulphonylation may occur. In this situation, one of the $CH_3SO_2$— substituents can be removed by reaction of the di-sulphonylated product with aqueous sodium hydroxide. Compounds of formula IV are known or can be prepared by known techniques (see for example PCT/EP95/03559).

In the synthesis of the compounds of the invention it may be necessary or desirable to protect sensitive functional groups and then deprotect them. Methods for such operations are known to those skilled in the art and are described in 'Protective Groups in Organic Synthesis' mentioned above.

The compounds of the invention are useful because they possess pharmacological activity in animals (including humans). In particular, the compounds are useful in the treatment or prevention of neurodegenerative disorders (including senile dementia, Alzheimer's disease and those arising from events such as stroke, transient ischaemic attack, peri-operative ischaemia and traumatic head injury to the brain or spinal cord; and retinal and macular degeneration), convulsions, pain and anxiety. The treatment of stroke is of particular interest. The compounds may also be useful in the treatment of tinnitus.

Thus, according to another aspect of the invention, there is provided an anxiolytic, anticonvulsant, analgesic or neuroprotective method of treatment, which comprises administration of a compound of the invention to a patient in need of such treatment. The use of the compounds of the invention as pharmaceuticals, and the use of the compounds of the invention in the manufacture of an anxiolytic, anticonvulsant, analgesic or neuroprotective medicament, are also provided.

The biological activity of the compounds of the invention may be demonstrated in the tests set out below:

(a) Binding affinity for the glycine site of the NMDA receptor

This may be measured by testing a compound's ability to displace a selective glycine site radioligand from rat brain membranes as described in Brit J Pharm (1991), 104, 74. In a variation of this method, thoroughly washed membrane protein is incubated with [$^3$H]-L-689,560 for 90 minutes using tris-acetate buffer (pH 7.4). Displacement of the radioligand, using a range of test compound concentrations, is used to derive $IC_{50}$ (50% inhibitory concentration) values.

(b) Binding affinity for the AMPA receptor

This may be measured by testing a compound's ability to displace the radioligand [$^3$H]-AMPA from rat brain membranes. Membrane homogenate is incubated with radioligand (10 nM) in the presence or absence of test compounds at various concentrations at 4° C. for 45 min. Free and bound radiolabel is separated by rapid filtration, and radioactivity is measured by liquid scintillation counting.

(c) Functional in vitro NMDA antagonism

This is demonstrated by the ability of a compound to inhibit the depolarizations in rat cortical slices induced by NMDA, similar to the method described in J Med Chem, (1990), 33, 789 and Brit J Pharm (1985), 84, 381. In a variation of the procedure, the response to a standard concentration of NMDA is measured in the presence of a range of test compound concentrations, and the results obtained are used to derive $IC_{50}$ (50% inhibitory concentration) values.

(d) NMDA antagonism in vivo

This can be demonstrated by the ability of a compound to inhibit NMDA-induced wild running in the mouse according to a variation of the method described in Brit J Pharm Proceedings Supplement (1992), 107, 58P. In this model, groups of mice are treated with test compounds at various doses prior to administration of NMDA (60 mg/kg i.v.). The latency of onset of wild running is recorded and the presence or absence of this behaviour used to determine an $ED_{50}$. Probit analysis is used to estimate a dose at which 50% of mice fail to display wild running by 10 minutes post NMDA administration.

(e) Blocking of cortical spreading depression

In vivo activity of a compound may also be demonstrated by measuring its ability to block the propagation of electrically-initiated cortical spreading depression in anaesthetised rats. Thus, male rats are anaesthetised and two glass microelectrodes are inserted into the right parietal cortex to a depth of 0.5–1mm for recording brain activity. In addition, a bipolar stimulating electrode is placed on the dura in front of the microelectrodes. The dura is then electrically stimulated at 10 minute intervals, and the waves of spreading depression are detected by the microelectrodes, amplified and displayed using a chart recorder. Test compounds are dissolved in water as their sodium salts, or hydrochloride salts (where possible) and administered by i.v. injection at various doses to determine the minimum dose which blocks the propagation of the spreading depression.

The compounds of the invention may be administered to a patient in need of treatment by a variety of conventional routes of administration, including oral and intravenous administration. The compounds have potential for absorption through the gastrointestinal tract and thus administration by slow release formulations is also possible.

In general, a therapeutically-effective oral dose is likely to range from 0.1 to 100 mg/kg body weight of the subject to be treated, preferably 1 to 10 mg/kg, and an intravenous dose is likely to range from 0.01–10 mg/kg of body weight of subject treated, preferably 0.1–5 mg/kg. Where necessary, the compounds may also be administered by intravenous infusion, at a dose which is likely to range from 0.01–1 mg/kg/hr. In practice the physician will determine the actual dosage which will be most suitable for an individual patient and it will vary with age, weight and response of the particular patient. The above dosages are exemplary of the average case but there can, of course, be individual instances where higher or lower dosage ranges are merited, and such are within the scope of the invention.

Although the compounds of the invention can be administered alone, they will generally be administered in admixture with a pharmaceutical carrier selected with regard to the intended route of administration and standard pharmaceutical practice. For example, oral administration may be in the form of tablets containing such excipients as starch or lactose, in capsules either alone or in admixture with excipients, or in the form of elixirs or suspensions containing flavouring or colouring agents. The compounds may be injected parenterally, for example intravenously, intramuscularly or subcutaneously. For parenteral administration they are best used in the form of a sterile aqueous solution of an appropriate salt of the compound and the solution may contain other substances such as salts to make it isotonic with blood.

Thus, there is further provided a pharmaceutical formulation comprising a compound of the invention, in admixture with a pharmaceutically acceptable adjuvant, diluent or carrier.

The compounds of the invention may have the advantage that they are more potent, more soluble, more selective [for example being potent antagonists of the NMDA (glycine site) receptor but with little or no affinity for the AMPA receptor], less toxic or possess other more desirable properties than the compounds of the prior art.

The invention is illustrated by the following Examples, in which the following abbreviations are used:

| APCI | atmospheric pressure chemical ionisation |
| DMF | dimethyl formamide |
| DMSO | dimethylsulphoxide |

Melting points were determined using a Buchi apparatus in glass capillary tubes and are uncorrected. Spectroscopic data were recorded on Perkin-Elmer 983 (Infra Red), Fisons Trio 1000 (Mass Spectrometer, thermospray using ammonium acetate in aqueous methanol as carrier), and Bruker AC300 and Varian Unity 300 NMR instruments (both 300 MHz), and were consistent with the assigned structures. Column chromatography was accomplished on Kieselgel 60, (230–400 mesh) from E. Merck, Darmstadt. Kieselgel 60 $F_{254}$ plates from E. Merck were used for thin layer chromatography (TLC), and compounds were visualised with UV light or chloroplatinic acid/potassium iodide solution. In cases where compounds analysed as hydrates, the presence of water was evident in the enhanced peak due to water in the proton NMR spectra. The purity of compounds was carefully assessed using analytical TLC and proton NMR (300 MHz), and the latter technique was used to calculate the amount of solvent in solvated samples. In multistep sequences, the purity and structure of intermediates were verified spectroscopically by proton NMR. Proton NMR shifts are quoted in parts per million downfield from tetramethylsilane.

EXAMPLE 1

N-(1,4-Dihydro-6,7-dichloro-2,3-dioxoquinoxalin-5-yl)-N-(2-(N'-methanesulphonyl)-aminoethyl)methanesulphonamide

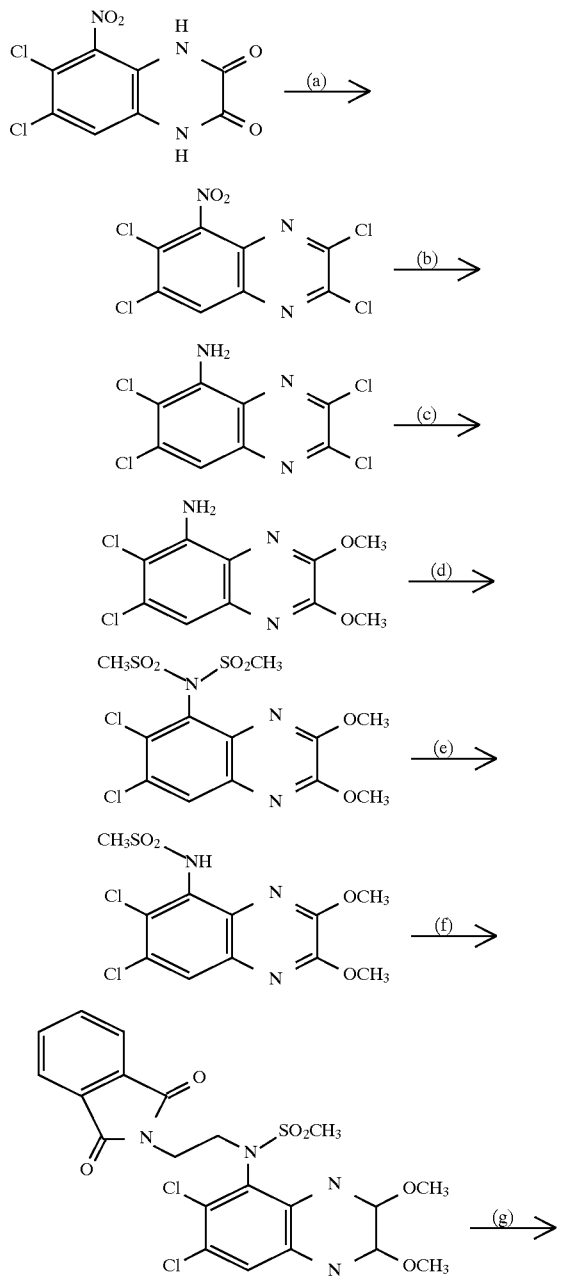

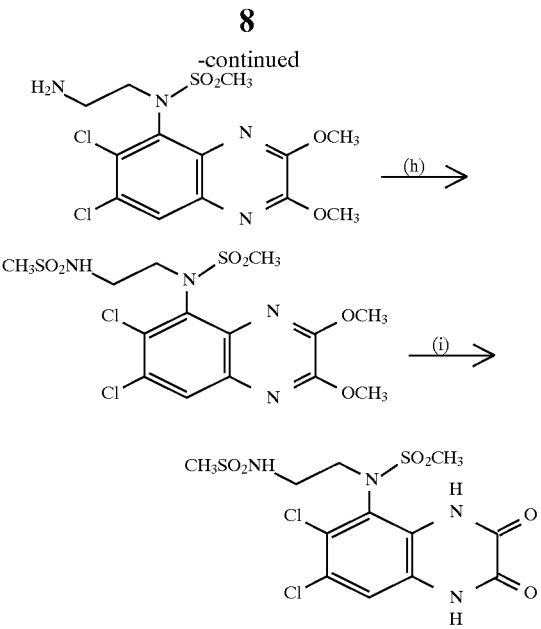

(a) A mixture of 6,7-dichloro-1,4-dihydro-5-nitroquinoxalin-2,3-dione (Example 1 of WO-A-94/00124, 84 g, 0.34 mol), thionyl chloride (840 ml) and dimethylformamide (0.5 ml) was heated at reflux for 3 hours, cooled and concentrated under reduced pressure. Ethyl acetate (300 ml) was added and removed under reduced pressure, followed by petroleum ether (bp 100°–120° C.). The solid residue was recrystallised from petroleum ether (bp 100°–120° C.) to give 2,3,6,7-tetrachloro-5-nitro-quinoxaline (78 g, 73%) as a light yellow solid.

$^1$H-NMR (300 MHz, CDCl$_3$): δ=8.6 (1H, s).

(b) Tin (II) chloride dihydrate (346.3 g, 1.54 mol) was added to a solution of 2,3,6,7-tetrachloro-5-nitro-quinoxaline (96.2 g, 0.31 mol) in ethyl acetate (1.8 l). The mixture was heated under reflux for 4 hours, cooled and poured cautiously into an excess of aqueous saturated sodium bicarbonate. The mixture was filtered through "Celite", (Trade Mark), washing well with ethyl acetate. The filter cake was macerated with more ethyl acetate and the solid material filtered off. The combined ethyl acetate solutions were dried (MgSO$_4$) and concentrated under reduced pressure to give 5-amino-2,3,6,7-tetrachloroquinoxaline (73.4 g, 84%) as a yellow solid.

$^1$H NMR (300 MHz, CDCl$_3$): δ=5.45 (2H, broad s), 7.47 (1H, s). m/z (thermospray) 385 (MH$^+$).

(c) A solution of sodium methoxide (25% solution in methanol, 274 ml, 1.28 mol) was added to a suspension of 5-amino-2,3,6,7-tetrachloroquinoxaline (72.4 g, 0.256 mol) in dry methanol (1 l) and the resulting mixture was heated at reflux for 30 minutes. The mixture was cooled, concentrated under reduced pressure, and the residue partitioned between water and ethyl acetate (total of 8 l). The organic solution was dried (MgSO$_4$) and concentrated under reduced pressure. The crude product was purified by trituration with methanol, followed by dissolution in dichloromethane (2 l) and filtration. The filtrate was concentrated under reduced pressure to give 5-amino-6,7-dichloro-2,3-dimethoxyquinoxaline as a yellow solid (55.0 g, 79%).

$^1$H NMR (300 MHz, CDCl$_3$): δ=4.13 (3H, s), 4.14 (3H, s), 5.07 (2H, broad s), 7.26 (1H, s). m/z (thermospray) 274 (MH$^+$).

(d) A mixture of 5-amino-6,7-dichloro-2,3-dimethoxyquinoxaline (10.0 g, 36.5 mmol), methanesulphonic anhydride (31.8 g, 183 mmol) and pyridine (14.8 ml, 183 mmol) in dry dichloromethane (150 ml) was stirred at 20° C. for 16 hours. The solvent was removed under reduced pressure and the residue dissolved in a mixture of water (5 ml) and tetrahydrofuran (50 ml). After being stirred for 10 minutes, the solution was partitioned between ethyl acetate and 2M hydrochloric acid. The combined organic solutions were washed with saturated aqueous sodium bicarbonate, dried (MgSO$_4$), and concentrated under reduced pressure. Purification of the residue by flash chromatography (gradient elution with hexane/dichloromethane) gave 6,7-dichloro-5-di(methanesulphonyl) amino-2,3-dimethoxyquinoxaline as an off-white solid (12.3 g, 78%), mp 240°–244° C.

$^1$H NMR (300 MHz, CDCl$_3$): δ=3.62 (6H, s), 4.16 (3H, s), 4.18 (3H, s), 8.02 (1H, s). m/z (thermospray) 430, 432 (MH$^+$).

(e) Aqueous sodium hydroxide (1M, 145 ml, 145 mmol) was added to a suspension of 6,7-dichloro-5-di(methanesulphonyl)amino-2,3-dimethoxy-quinoxaline (12.28 g, 28.6 mmol) and the mixture was stirred at room temperature for 16 hours. The resulting orange solution was treated with 2M hydrochloric acid (to pH 3) and the solid which precipitated was filtered off, washed with water and ether, and dried under reduced pressure at 80° C. to give N-(6,7-dichloro-2,3-dimethoxyquinoxalin-5-yl) methanesulphonamide (8.46 g, 84%) as a white solid, mp 225°–227° C.

$^1$H NMR (300 MHz, CDCl$_3$): δ=3.42 (3H, s), 4.15 (3H, s), 4.20 (3H, s), 7.15 (1H, broad s), 8.02 (1H, s). m/z (thermospray) 352 (MH$^+$).

(f) N-(2-bromoethyl)phthalimide (1.73 g, 6.81 mmol) was added to a refluxing mixture of N-(6,7-dichloro-2,3-dimethoxy-quinoxalin-5-yl)-methanesulphonamide (2.00 g, 5.68 mmol) and potassium carbonate (1.88 g, 13.63 mmol) in acetone (100 ml) under nitrogen. After 48 hours, further N-(2-bromoethyl)phthalimide (1.73 g, 6.81 mmol) was added and refluxing continued for 18 hours. After cooling the mixture was concentrated under reduced pressure and the residue dissolved in dichloromethane. The resulting solution was washed twice with 1N sodium hydroxide solution, water and brine and then dried (MgSO$_4$) and concentrated under reduced pressure. The residue was purified by flash chromatography (eluting with hexane:ethyl acetate) to afford N-(6,7-dichloro-2,3-dimethoxyquinoxalin-5-yl)-N-(2-phthalimidoethyl)methanesulphonamide as a pale yellow solid (2.55 g, 85%).

$^1$H NMR (300 MHz, CDCl$_3$) δ=3.25 (3H, s), 3.64 (2H, t, J 8Hz), 3.90–4.02 (2H, m), 4.12 (3H, s), 4.17 (3H, s), 7.65–7.80 (3H, m), 7.82–7.92 (2H, m). m/z (thermospray) 525 (MH$^+$).

(g) Hydrazine hydrate (696 μl, 716 mg, 14.3 mmol) was added dropwise to a solution of N-(6,7-dichloro-2,3-dimethoxyquinoxalin-5-yl)-N-(2-phthalimidoethyl) methanesulphonamide (3.76 g, 7.15 mmol) in a mixture of dichloromethane (71 ml) and methanol (5 ml) at room temperature under nitrogen. The mixture was heated at reflux for 4 days and then further methanol (20 ml) was added. After a further 2 days the mixture was allowed to cool and was concentrated under reduced pressure. The residue was dissolved in ethyl acetate and this was extracted 3 times with 10% aqueous citric acid. The combined acid extracts were adjusted to pH 9 with solid potassium carbonate and extracted 3 times with dichloromethane. The combined dichloromethane extracts were dried (MgSO$_4$) and concentrated under reduced pressure. The residue was purified by flash chromatography on silica gel eluting with 95:5 dichloromethane:methanol to give N-(6,7-dichloro-2,3-dimethoxyquinoxalin-5-yl)-N-(2-aminoethyl) methanesulphonamide (1.96 g, 69%) as a pale yellow solid.

$^1$H NMR (300 MHz, CDCl$_3$) δ=2.70–2.88 (2H, m), 3.11 (3H, s), 3.79 (2H, t, J 8Hz), 4.17 (3H, s), 4.20 (3H, s), 7.95 (1 H, s). m/z (thermospray) 395 (MH$^+$).

(h) A mixture of N-(6,7-dichloro-2,3-dimethoxyquinoxalin-5-yl)-N-(2-aminoethyl)-methanesulphonamide (250 mg, 0.632 mmol), pyridine (61 μl, 60 mg, 0.759 mmol) and methanesulphonic anhydride (132 mg, 0.759 mmol) in dry tetrahydrofuran (6.5 ml) was stirred at room temperature under nitrogen for 2 days. Further pyridine (61 μl, 60 mg, 0.759 mmol) and methanesulphonic anhydride (132 mg, 0.759 mmol) were added and stirring continued for a further 2 days. This was repeated again and after another 2 days pyridine (122 μl, 120 mg, 1.518 mmol) and methanesulphonic anhydride (264 mg, 1.518 mmol) were added. After another 2 days (8 days in total) water was added and the mixture was partitioned between water and ethyl acetate. The organic layer was washed with 2M hydrochloric acid, water, saturated sodium bicarbonate solution, water and brine and then dried (MgSO$_4$) and concentrated under reduced pressure to give N-(6,7-dichloro-2,3-dimethoxyquinoxalin-5-yl)-N-(2-(N'-methanesulphonyl)-aminoethyl)methanesulphonamide (116 mg, 39%).

$^1$H NMR (300 MHz, CDCl$_3$) δ=2.90 (3H, s), 3.16 (1H, m), 3.21 (3H, s), 3.37 (1H, m), 4.00 (2H, m), 4.18 (3H, s), 4.21 (3H, s), 5.60 (1H, s), 7.99 (1H, s). m/z (thermospray) 473 (MH$^+$).

(i) A mixture of N-(6,7-dichloro-2,3-dimethoxyquinoxalin-5-yl)-N-(2-(N'-methanesulphonyl) aminoethyl)methanesulphonamide (112 mg, 2.37 mmol), 2M hydrochloric acid (1.2 ml) and 1,4-dioxan (2.5 ml) was heated at reflux for 18 hours. After cooling the mixture was concentrated under reduced pressure and the residue triturated with ether and the resulting solid collected by filtration and dried under reduced pressure at 60° C. The title compound (70 mg, 66%) was obtained as a foam.

$^1$H NMR (300 MHz, DMSO-d$_6$) δ=2.84 (3H, s), 3.16 (2H, m), 3.23 (3H, s), 3.79 (2H, m), 7.02 (1H, s), 7.40 (1H, s), 10.55 (1H, s), 12.10 (1H, s). m/z (thermospray) 462 (MNH$_4^+$).

EXAMPLE 2

N-(1,4-Dihydro-6,7-dichloro-2,3-dioxoquinoxalin-5-yl)-N-(2-(N'-4-(1H-1-methylimidazolyl) sulphonyl) aminoethyl)methanesulphonamide

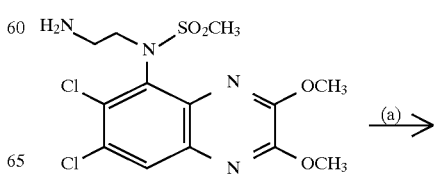

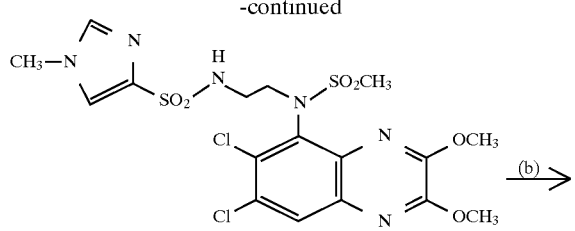

(a) A mixture of N-(6,7-dichloro-2,3-dimethoxyquinoxalin-5-yl)-N-(2-aminoethyl)-methanesulphonamide (Example 1 step (g), 200 mg, 0.506 mmol), pyridine (49 μl, 48 mg, 0.607 mmol) and 1-methylimidazole-4-sulphonyl chloride (110 mg, 0.607 mmol) in dry dichloromethane (5 ml) was stirred at room temperature under nitrogen for 24 hours. Further pyridine (49 μl, 48 mg, 0.607 mmol) and 1-methylimidazole-4-sulphonyl chloride (110 mg, 0.607 mmol) were added and stirring continued for a further 3 days. The mixture was washed with water, 2M hydrochloric acid, water, saturated sodium bicarbonate solution, water and brine and then dried (MgSO$_4$) and concentrated under reduced pressure. The residue was purified by flash chromatography on silica gel eluting with 95:5 dichloromethane:methanol to give N-(6,7-dichloro-2,3-dimethoxyquinoxalin-5-yl)-N-(2-(N'-4-(1H-1-methylimidazolyl)sulphonyl) aminoethyl) methanesulphonamide (203 mg, 74%).

$^1$H NMR (300 MHz, CDCl$_3$) δ=3.05 (1H, m), 3.22 (3H, s), 3.28 (1H, m), 3.66 (3H, s), 4.00 (2H, m), 4.18 (3H, s), 4.24 (3H, s), 6.00 (1H, s), 7.21 (1H, s), 7.26 (1H, s, obscured), 7.96 (1H, s). m/z (thermospray) 539 (MH$^+$).

(b) The title compound was prepared from N-(6,7-dichloro-2,3-dimethoxyquinoxalin-5-yl)-N-(2-(N'-4-(1-methylimidazolyl) sulphonyl)-aminoethyl) methanesulphonamide (198 mg, 0.387 mmol) by the method of Example 1 step (i) and was obtained as a foam (119 mg, 63%).

Analysis %: Found, C, 31.14; H, 3.51; N, 14.12. C$_{15}$H$_{16}$Cl$_2$N$_6$O$_6$S$_2$. HCl. 2H$_2$O requires: C, 30.86; H, 3.63; N, 14.39.

EXAMPLE 3

N-(Carboxymethyl)-N-(1,4-dihydro-7-chloro-6-methyl-2,3-dioxoquinoxalin-5-yl) methanesulphonamide

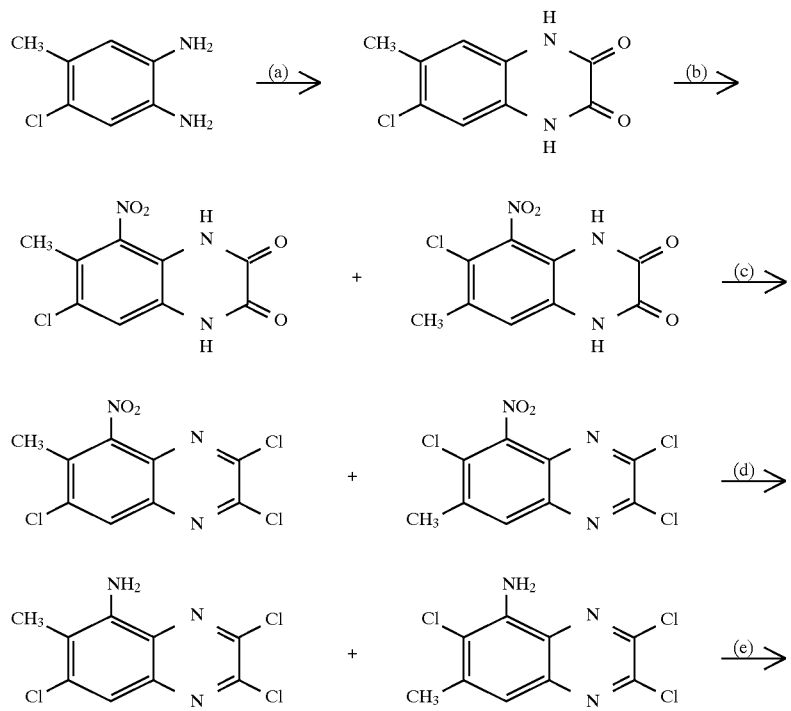

-continued

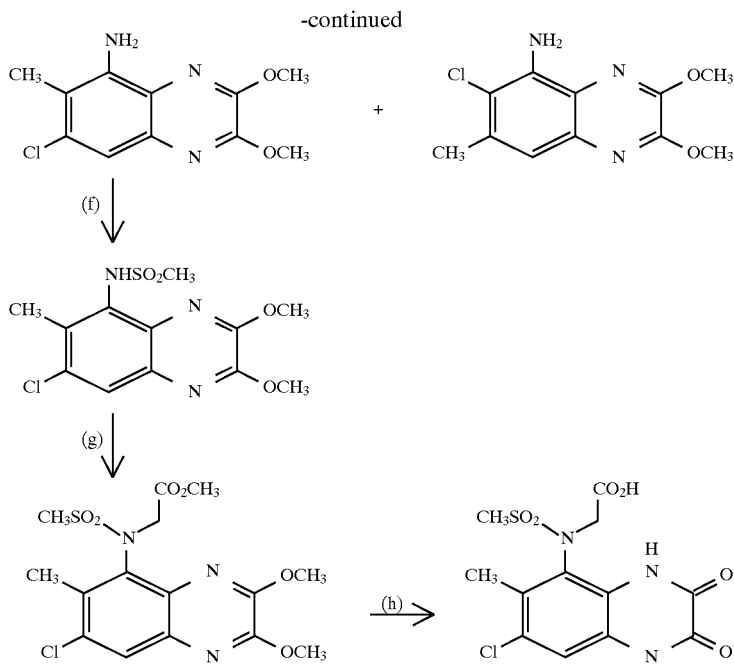

(a) A mixture of 1,2-diamino-4-chloro-5-methylbenzene hydrochloride [J Chem Soc, 117, 784 (1920)] (1.90 g, 9.84 mmol), oxalic acid (1.24 g, 13.8 mmol) and 4M hydrochloric acid (49 ml) was heated at reflux for 4.5 hours. After cooling the solid precipitate was collected by filtration, washed well with water and dried under reduced pressure at 80° C. to afford 1,4-dihydro-6-chloro-7-methylquinoxalin-2,3-dione (1.68 g, 81%) as a dark grey solid, mp>330° C.

Analysis %: Found; C, 51.58; H, 2.98; N, 13.27. $C_9H_7ClN_2O_2$ requires C, 51.32; H, 3.35; N, 13.30.

(b) 1,4-dihydro-6-chloro-7-methylquinoxalin-2,3-dione (1.26 g, 5.98 mmol) was added in portions over 3 minutes to vigorously stirred conc. nitric acid at room temperature. The resulting heterogeneous mixture was then warmed to 40° C. and stirred for 12 hours. After cooling the yellow mixture was poured into ice-water (100 ml) and this was stirred for 30 minutes. The resulting yellow precipitate was collected by filtration, washed with water and dried by suction to afford a mixture of 1,4-dihydro-6-chloro-7-methyl-5-nitroquinoxalin-2,3-dione and 1,4-dihydro-7-chloro-6-methyl-5-nitroquinoxalin-2,3-dione (1:2 ratio, 1.35 g, 88%) as a yellow solid.

$^1$H NMR (300 MHz, CDCl$_3$) δ=2.23 (2H, s), 2.35 (1H, s), 7.19 (0.3H, s), 7.30 (0.7H, s), 11.9–12.25 (2H, broad m).

(c) A mixture of 1,4-dihydro6-chloro-7-methyl-5-nitroquinoxalin-2,3-dione and 1,4-dihydro-7-chloro-6-methyl-5-nitroquinoxalin-2,3-dione (1.35 g, 5.73 mmol), thionyl chloride (12.5 ml, 20.4 g, 0.172 mmol) and dimethylformamide (44 μl, 42 mg, 0.573 mmol) was heated at reflux for 4¼ hours producing a clear yellow solution. After cooling the mixture was cautiously added to vigorously stirred ice-water (300 ml). The resulting precipitate was collected by filtration, washed with water and dried by suction to give a mixture of 2,3,7-trichloro-6-methyl-5-nitroquinoxal and 2,3,6-trichloro-7-methyl-5-nitroquinoxaline (2:1 ratio, 1.45 g, 87%) as a straw-coloured powder. This mixture could be separated with difficulty for characterisation purposes by flash chromatography (gradient elution with hexaneldichloromethane) to give first 2,3,7-trichloro-6-methyl-5-nitroquinoxaline as a white solid, mp 164°–165° C.

Analysis %: Found, C,36.76; H,1.37; N,14.43. $C_9H_4Cl_3N_3O_2$ requires: C, 36.96; H, 1.38; N, 14.37.

The second eluted isomer, 2,3,6-trichloro-7-methyl-5-nitro-quinoxaline was obtained as a straw-coloured solid, mp 121°–122° C.

Analysis %: Found, C, 39.78; H, 2.02; N, 13.23. $C_9H_4Cl_3N_3O_2$. 0.22 hexane requires: C, 39.80; H, 2.29; N, 13.49.

(d) A mixture of 2,3,7-trichloro-6-methyl-5-nitroquinoxaline and 2,3,6-trichloro-7-methyl-5-nitroquinoxaline (250 mg, 0.855 mmol) and stannous chloride dihydrate (1.35 g, 5.98 mmol) in ethyl acetate (8.5 ml) was heated at reflux for 3 hours under nitrogen. After cooling the mixture was diluted with ethyl acetate (50 ml) and washed with 10% aqueous sodium carbonate solution (2×25 ml) and brine (25 ml) and then dried (MgSO$_4$), filtered and concentrated under reduced pressure to afford a mixture of 5-amino-2,3,7-trichloro-6-methylquinoxaline and 5-amino-2,3,6-trichloro-7-methylquinoxaline (217 mg, 97%) as an orange solid.

$^1$H NMR (300 MHz, CDCl$_3$) δ=2.41 (2H, s), 2.55 (1H, s), 5.03 (1.3H, broad s), 5.08 (0.7H, broad s), 7.23 (0.3H, s), 7.44 (0.7H, s). m/z (thermospray) 262 (MH$^+$).

(e) A 25% solution of sodium methoxide in methanol (433 μl, 1.89 mmol) was added dropwise to a solution of 5-amino-2,3,7-trichloro-6-methylquinoxaline and 5-amino-2,3,6-trichloro-7-methylquinoxaline (200 mg, 0.788 mmol) in dry tetrahydrofuran (7.9 ml) at 0° C. under nitrogen. The mixture was stirred for 3¼ hours and then diluted with ethyl acetate (30 ml) and washed with water (2×10 ml) and brine (10 ml) and then dried (MgSO$_4$) filtered and concentrated under reduced pressure. The solid residue was purified by flash chromatography on silica gel, eluting with a hexane/ethyl acetate gradient giving 5-amino-6-chloro-2,3-dimethoxy-7-methylquinoxaline as an off-white solid, mp 169°–170° C.

Analysis %: Found, C, 53.80; H, 5.16; N, 16.18. $C_{11}H_{12}ClN_3O_2$. 0.15 hexane requires: C, 53.61; H, 5.33; N, 15.76. The second eluted compound, 5-amino-7-chloro-2,3- dimethoxy-6-methylquinoxaline, was obtained as an orange solid, mp 181°–182° C.

Analysis %: Found, C, 52.55; H, 4.72; N, 16.61. $C_{11}H_{12}ClN_3O_2$. 0.05 hexane requires: C, 52.61; H, 4.96; N, 16.29.

(f) Pyridine (80 μl, 78 mg, 0.985 mmol) and methanesulphonic anhydride (172 mg, 0.985 mmol) were added to a solution of 5-amino-7-chloro-2,3-dimethoxy-6-methylquinoxaline (50 mg, 0.197 mmol) in dry tetrahydrofuran (1.6 ml) at room temperature under nitrogen. After stirring for 17 hours water (0.3 ml) was added and stirring continued for 1 hour. The mixture was diluted with ethyl acetate (15 ml) and washed with 2M hydrochloric acid (5 ml), water(5 ml), saturated sodium bicarbonate solution (5 ml) and brine (5 ml) and then dried (MgSO$_4$), filtered and concentrated under reduced pressure to afford N-(7-chloro-2,3-dimethoxy-6-methylquinoxalin-5-yl) methanesulphonamide (66 mg, 100%) as a white solid mp 228°–229° C.

Analysis %: Found, C, 43.51; H, 3.98; N, 12.60. $C_{12}H_{14}ClN_3O_4S$ requires: C, 43.44; H; 4.25; N, 12.60.

(g) A mixture of N-(7-chloro-2,3-dimethoxy-6-methylquinoxalin-5-yl)methanesulphonamide (694 mg, 2.09 mmol), potassium carbonate (347 mg, 2.51 mmol) and acetone (21 ml) was heated at reflux for 10 minutes and was then allowed to cool to room temperature. Methyl bromoacetate (396 μl, 640 mg, 4.19 mmol) was added and the mixture was heated at reflux for 18 hours. The mixture was allowed to cool to room temperature and was concentrated under reduced pressure. The residue was dissolved in dichloromethane and washed twice with water and then brine and then dried (MgSO$_4$) and concentrated under reduced pressure. The residue was purified by flash chromatography on silica gel eluting with dichloromethane to give N-(7-chloro-2,3-dimethoxy-6-methylquinoxalin-5-yl)-N-(methoxycarbonylmethyl)methanesulphonamide as a white solid (407 mg, 48%).

$^1$H NMR (300 MHz, CDCl$_3$) δ=2.73 (3H, s), 3.18 (3H, s), 3.72 (3H, s), 4.13 (3H, s), 4.19 (3H, s), 4.20 (1H, d, J 19Hz), 4.79 (1H, d, J 19Hz), 7.85 (1H, s). m/z (thermospray) 404 (MH$^+$).

(h) The title compound was prepared from N-(7chloro-2,3-dimethoxy-6-methylquinoxalin-5-yl)-N-(methoxycarbonylmethyl)methanesulphonamide (404 mg, 1.00 mmol) by the method of Example 1 step (i) but triturating with water in place of ether and was obtained as a white solid (283 mg, 78%) mp>300° C.

Analysis %: Found, C, 40.18; H, 3.47; N, 11.25. $C_{12}H_{12}ClN_3O_6S$ requires: C, 39.84; H, 3.34; N, 11.65.

EXAMPLE 4

N-(1,4-Dihydro-7-chloro-6-methyl-2,3-dioxoquinoxalin-5-yl)-N-(2-(N'-methanesulphonyl)-aminoethyl)methanesulphonamide

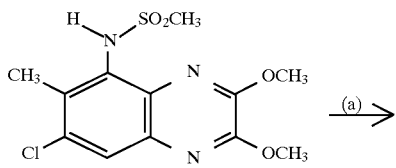

-continued

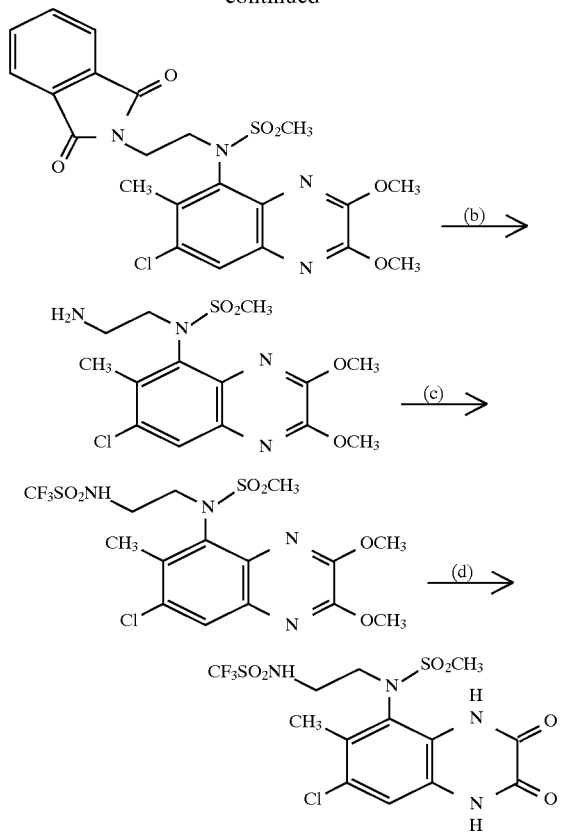

(a) N-(7-Cholro-6-methyl-2,3-dimethoxyquinoxalin-5-yl)-N-(2phthalimidoethyl)-methanesulphonamide was prepared from N-(7-chloro-6-methyl-2,3-dimethoxy-quinoxalin-5-yl)-methanesulphonamide (Example 3 step (f), 2.00 g, 5.68 mmol) by the method of Example 1 step (f) and was obtained as a solid (4.57 g, 47%).

$^1$H NMR (300 MHz, CDCl$_3$)δ=2.63 (3H, s), 3.12 (3H, s), 3.90 (2H, m), 4.08 (3H, s), 4.14 (3H, s), 4.25 (2H, t, J 4 Hz), 7.69 (4H, m), 7.79 (1H, s). m/z (thermospray) 505.6 (MH$^+$).

(b) N-(7-chloro-6-methyl-2,3-dimethoxyquinoxalin-5-yl)-N-(2-aminoethyl)-methanesulphonamide was prepared from N-(7-chloro-6-methyl-2,3-dimethoxyquinoxalin-5-yl)-N-(2-phthalimidoethyl)methanesulphonamide (4.57 g, 9.05 mmol) by the method of Example 1 step (g) and was obtained as a pale yellow solid (2.89 g, 85%).

$^1$H NMR (300 MHz, CDCl$_3$)δ=2.62 (3H, s), 2.81 (2H, m), 3.18 (3H, s), 3.89 (2H, t, J 4 Hz), 4.16 (6H, s), 7.88 (1H, s). m/z (thermospray) 375.4 (MH$^+$).

(c) Trifluromethanesulphonic anhydride (99 μl, 166 mg, 0.587 mmol) was added to a solution of N-(7chloro-6-methyl-2,3-dimethoxyquinoxalin-5-yl)-N-(2-aminoethyl) methanesulphonamide (200 mg, 0.534 mmol) and triethylamine (53 μl, 35 mg, 0.587 mmol) in dry dichloromethane (5 ml) at −78° C. under nitrogen. The mixture was stirred for 1 hour at −78° C. and was then allowed to warm to room temperature and was stirred for 18 hours. The reaction mixture was washed with water, saturated sodium bicarbonate solution, water and brine and then dried (MgSO$_4$), filtered and concentrated under reduced pressure to yield a pale yellow solid (149 mg). The solid was suspended in 1,4-dioxan (2 ml) and 1M sodium hydroxide (1.2 ml) was added dropwise. The resulting solution was stirred for 1 hour and was then neutralised to pH 7 with 2M hydrochloric acid and concentrated under reduced pressure. The residue was partitioned between dichloromethane and water and the organic layer was washed with water and brine and dried (MgSO$_4$), filtered and concentrated under reduced pressure to yield N-(7-chloro-6-methyl-2,3-dimethoxyquinoxalin-5-yl)-N-(2-(N'-trifluoromethanesulphonyl)aminoethyl)-methanesulphonamide as a white solid (100 mg, 37%).

$^1$H NMR (300 MHz, CDCl$_3$) δ=2.60 (3H, s), 3.19 (3H, m), 3.29 (1H, s), 3.50 (1H, m), 3.91 (1H, m), 4.08 (1H, m), 4.18 (6H, s), 7.92 (1H, s). m/z (thermospray) 507.5 (MH$^+$).

(d) The title compound was prepared from N-(7-chloro-6-methyl-2,3-dimethoxyquinoxalin-5-yl)-N-(2-(N'-trifluoromethanesulphonyl)aminoethyl) methanesulphonamide (100 mg, 0.197 mmol) by the method of Example 1 step (i) and was obtained as an off-white foam (62 mg, 66%).

$^1$H NMR (300 MHz, CDCl$_3$) δ=2.30 (3H, s), 3.15 (2H, m, obscured), 3.23 (3H, s), 3.71 (2H, t, J 7 Hz), 7.22 (1H, s), 9.38 (1H, s), 10.58 (1H, s), 11.96 (1H, s). m/z (thermospray) 495.7 (MNH$_4^+$).

EXAMPLE 5

(+)- and (-)-N-(Carboxymethyl)-N-(1,4-dihydro-6-chloro-7-methyl-2,3-dioxoquinoxalin-5-yl) methanesulphonamide

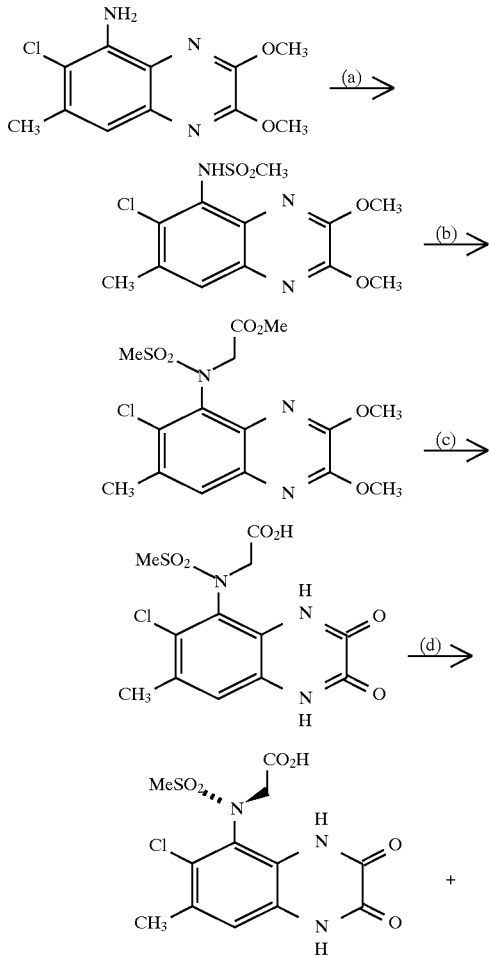

-continued

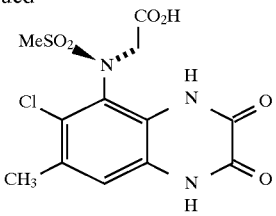

(a) Pyridine (80 μl, 78 mg, 0.985 mmol) and methanesulphonic anhydride (172 mg, 0.985 mmol) were added to a solution of 5-amino-6-chloro-2,3-dimethoxy-7-methylquinoxaline (Example 3 step (e), 50 mg, 0.197 mmol) in dry tetrahydrofuran (1.6 ml) at room temperature under nitrogen. After stirring for 24 hours further pyridine (32 μl, 31 mg, 0.394 mmol) and methanesulphonic anhydride (69 mg, 0.394 mmol) were added. After a further 16 hours water (0.6 ml) was added and stirring continued for 1 hour. The mixture was diluted with ethyl acetate (15 ml) and washed with 2M hydrochloric acid (5 ml), water (5 ml), saturated sodium bicarbonate solution (5 ml) and brine (5 ml) and then dried (MgSO$_4$), filtered and concentrated under reduced pressure. The solid residue was purified by flash chromatography on silica gel eluting with 3:1 hexane:ethyl acetate to give N-(6-chloro-2,3-dimethoxy-7-methylquinoxalin-5-yl)methanesulphonamide (55 mg, 84%) as a white solid mp 198° C.

$^1$H NMR (300 MHz, CDCl$_3$) δ=2.58, (3H, s), 3.38 (3H, s), 4.15 (3H, s), 4.18 (3H, s), 7.00 (1H, broad s), 7.60 (1H, s). m/z (thermospray) 332 (MH$^+$). ν$_{max}$ (KBr) 3230, 2950, 1480 and 1150 cm$^{-1}$.

(b) N-(6-Chloro-2,3-dimethoxy-7-methylquinoxalin-5-yl)-N-(methoxycarbonylmethyl)methanesulphonamide was prepared from N-(6-chloro-2,3-dimethoxy-7-methylquinoxalin-5-yl)methanesulphonamide (641 mg, 1.93 mmol) by the method of Example 3 step (g) and was obtained after an additional trituration with ether as a solid (364 mg, 47%).

$^1$H NMR (300 MHz, CDCl$_3$) δ=2.58 (3H, s), 3.40 (3H, s), 3.70 (3H, s), 4.13 (3H, s), 4.20 (3H, s), 4.41 (1H, d, J 19 Hz), 4.47 (1H, d, J 19 Hz), 7.69 (1H, s). m/z (thermospray) 404 (MH$^+$).

(c) (±)-N-(Carboxymethyl)-N-(1,4-dihydro-6-chloro-7-methyl-2,3-dioxo-quinoxalin-5-yl)methanesulphonamide was prepared from N-(6-chloro-2,3-dimethoxy-7-methylquinoxalin-5-yl)-N-(methoxycarbonylmethyl) methanesulphonamide (360 mg, 0.892 mmol) by the method of Example 1 step (i) but triturating with water in place of ether and was obtained as a white solid (300 mg, 93%) mp>300° C.

Analysis %: Found, C, 37.28; H, 3.80; N, 10.83. C$_{12}$H$_{12}$ClN$_3$O$_6$S. 1.5H$_2$O requires: C, 37.07; H, 3.89; N. 10.81.

(d) Quinine trihydrate (1.38 g, 3.66 mmol) was added to a boiling suspension of N-(carboxymethyl)-N-(1,4-dihydro-6-chloro-7-methyl-2,3-dioxoquinoxalin-5-yl) methanesulphonamide (1.39 g, 3.66 mmol) in methanol (110 ml) and the mixture was boiled for 30 minutes. The resulting precipitate was collected by filtration from the hot mixture, washed well with methanol and dried under reduced pressure at 80° C. to give a white solid (1.05 g) which was recrystallised from methanol and dried under reduced pressure at 60° C. to leave a single diastereoisomeric quinine salt (698 mg, 28%), mp 279°–280° C.

Analysis %: Found, C, 55.51; H, 5.28; N, 10.05. $C_{32}H_{36}ClN_5O_8S$. $0.4H_2O$ requires: C, 55.43; H, 5.35; N, 10.10. $[\alpha]_D^{25} = -142°$ (c=0.1, Ethanol).

Concentrated hydrochloric acid (2 ml) was added to a stirred suspension of the quinine salt (mp 279°–280° C.) (572 mg, 0.773 mmol) in water (40 ml) at room temperature and the mixture stirred for 1 hour. The solid was collected by filtration, washed with water and dried under reduced pressure at 80° C. to give the first title compound (240 mg, 86%) as a white crystalline solid, mp 304°–305° C. (decomposes).

Analysis %: Found, C, 38.87; H, 3.52; N, 10.97. $C_{12}H_{12}ClN_3O_6S$. $0.5H_2O$ requires: C, 38.87; H, 3.53; N, 11.33. $[\alpha]_{546}^{25} = +3.00°$ (c=0.1, Ethanol).

The filtrate from the salt formation was concentrated to a volume of 80ml and then stirred at room temperature for 2 hours. A crystalline solid formed and was collected by filtration, washed with methanol and dried under reduced pressure at 80° C. to give a white solid (611 mg) which was recrystallised from methanol and dried under reduced pressure at 60° C. to give a second diastereoisomeric quinine salt (295 mg, 12%), mp 230°–232° C.

Analysis %: Found, C, 55.40; H, 5.39; N, 10.11. $C_{32}H_{36}ClN_5O_8S$. $0.4H_2O$ requires: C, 55.43; H, 5.35; N, 10.10. $[\alpha]_D^{25} = -117°$ (c=0.1, Ethanol).

Concentrated hydrochloric acid (2 ml) was added to a stirred suspension of the second quinine salt (mp 230°–232° C.) (616 mg, 0.832 mmol) in water (40 ml) at room temperature and the mixture stirred for 30 minutes. The solid was collected by filtration, washed with water and dried under reduced pressure at 80° C. to give the second title compound (276 mg, 92%) as a white crystalline solid, mp 302°–304° C. (decomposes).

Analysis %: Found, C, 38.48; H, 3.58; N, 11.27. $C_{12}H_{12}ClN_3O_6S$. $0.75H_2O$ requires: C, 38.41; H, 3.63; N, 11.20. $[\alpha]_{546}^{25} = -3.00°$ (c=0.1, Ethanol).

EXAMPLE 6

N-(1,4-Dihydro-6-chloro-7-methyl-2,3-dioxoquinoxalin-5-yl)-N-(2-(N'-methanesulphonyl)aminoethyl)methanesulphonamide

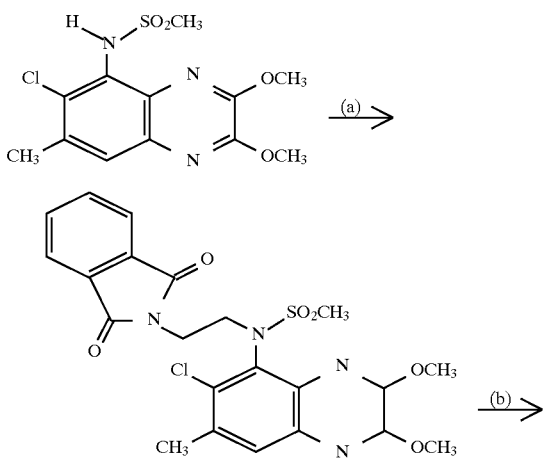

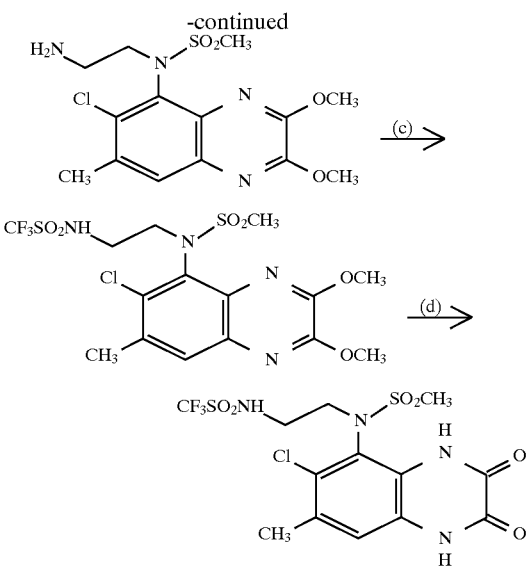

(a) N-(6-Chloro-2,3-dimethoxy-7-methylquinoxalin-5-yl)-N-(2-phthalimidoethyl)methanesulphonamide was prepared from N-(6-chloro-2,3-dimethoxy-7-methylquinoxalin-5-yl)-methanesulphonamide (Example 5 step (a), 3.41 g, 10.3 mmol) by the method of Example 1 step (f) but also adding sodium iodide (1.54 g, 10.3 mmol) to the reaction mixture and was obtained as a solid (4.12 g, 79%).

$^1$H NMR (300 MHz, $CDCl_3$) δ=2.52 (3H, s), 3.23 (3H, s), 3.98 (2H, m), 4.10 (3H, s) 4.12 (3H, s), 4.20 (2H, m), 7.71 (5H, m). m/z (thermospray) 504.7 ($MH^+$).

(b) N-(6-Chloro-2,3-dimethoxy-7-methylquinoxalin-5-yl)-N-(2-aminoethyl)-methanesulphonamide was prepared from N-(6-chloro-2,3-dimethoxy-7-methylquinoxalin-5-yl)-N-(2-phthalimidoethyl)methanesulphonamide (4.12 g, 8.16 mmol) by the method of Example 1 step (g) and was obtained as white solid (2.29 g, 69%).

$^1$H NMR (300 MHz, $CDCl_3$) δ=2.58 (3H, s), 2.80 (2H, m), 3.20 (3H, s), 3.86 (2H, t, J 4 Hz), 4.17 (3H, s), 4.19 (3H, s), 7.70 (1H, s). m/z (thermospray) 375.1 ($MH^+$).

(c) N-(6-Chloro-2,3-dimethoxy-7-methylquinoxalin-5-yl)-N-(2-(N'-trifluoromethanesulphonyl)aminoethyl)methanesulphonamide was prepared from N-(6-chloro-2,3-dimethoxy-7-methylquinoxalin-5-yl)-N-(2-aminoethyl)methanesulphonamide (200 mg, 0.534 mmol) by the method of Example 4 step (c) and was obtained as a pale yellow solid (265 mg, 98%).

$^1$H NMR (300 MHz, $CDCl_3$) δ=2.58 (3H, s), 3.19 (3H, m), 3.23 (1H, m), 3.58 (1H, m), 3.92 (1H, m), 4.12 (1H, m), 4.19 (3H, s), 4.22 (3H, s), 7.78 (1H, s). m/z (thermospray) 506.6 ($MH^+$).

(d) The title compound was prepared from N-(6-chloro-2,3-dimethoxy-7-methylquinoxalin-5-yl)-N-(2-(N'-trifluoromethanesulphonyl)aminoethyl)-methanesulphonamide (264 mg, 0.521 mmol) by the method of Example 1 step (i) and was obtained as an off-white foam 169 mg, 68%).

Analysis %: Found, C, 31.68; H, 3.68; N, 10.76. $C_{13}H_{14}ClF_3N_4O_6S$. $1.5H_2O$. $0.2Et_2O$ requires: C, 31.83; H, 3.68; N, 10.76.

EXAMPLE 7

N-(Carboxymethyl)-N-(1,4dihydro-6,7-dimethyl-2,3-dioxoquinoxalin-5-yl)methanesulphonamide

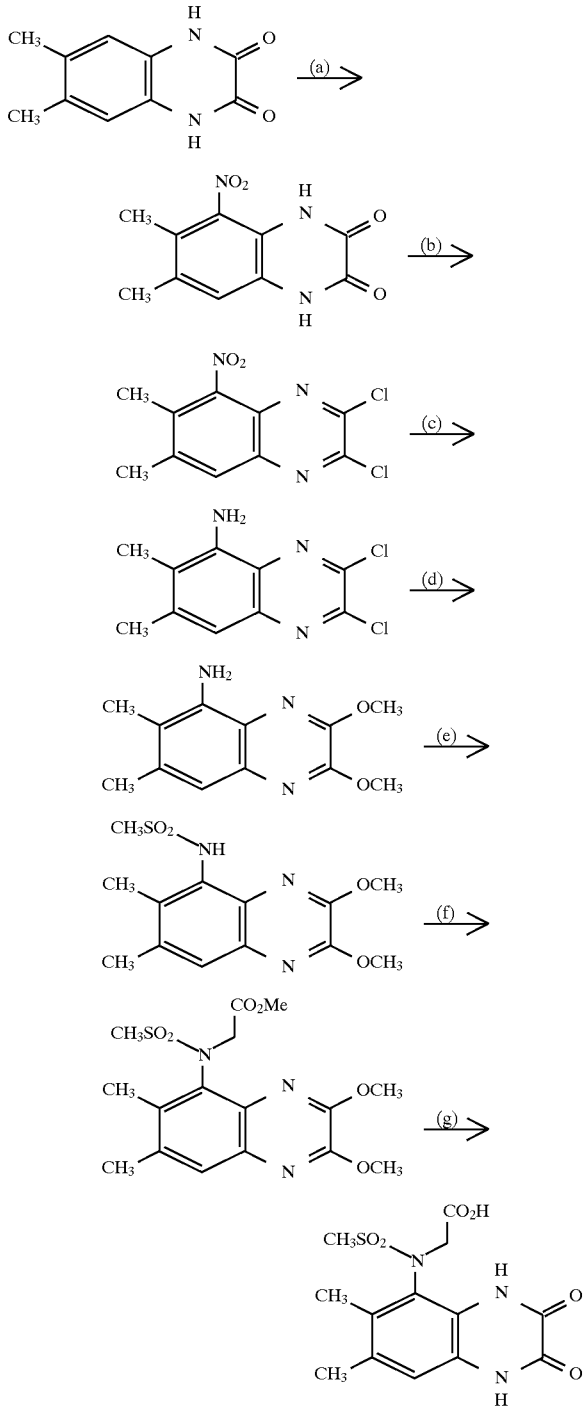

(a) 1,4-Dihydro-6,7-dimethylquinoxalin-2,3-dione (J. Liebigs Ann. Chem., 1982, 754–761, 10.0 g, 52.6 mmol) was added in portions over 10 minutes to concentrated nitric acid (density, 1.42 gcm$^{-3}$, 100 ml) at 0° C. After 5 minutes, the cooling bath was removed and the mixture was stirred at 20° C. for 7 hours, using cooling when necessary to maintain this temperature. The solution was poured into iced water, and the resulting solid filtered off and dried under reduced pressure at 75° C. to give 1,4-dihydro-6,7-dimethyl-5-nitroquinoxalin-2,3-dione (7.44 g, 60%) as a pale yellow solid, mp 280°–290° C. (dec.) (from dimethylformamide/water).

$^1$H NMR (300 MHz, DMSO-d$_6$): δ=2.08 (3H, s), 2.25 (3H, s), 7.06 (1H, s), 11.70 (1H, broad s), 12.06 (1H, broad s). v$_{max.}$ (KBr) 3185, 1703, 1533, 1400, 1355 cm$^{-1}$. m/z (thermospray) 253 (MNH$_4^+$).

(b) A mixture of 1,4-dihydro-6,7-dimethyl-5-nitroquinoxalin-2,3-dione (7.44 g, 31.6 mmol), thionyl chloride (69.2 ml, 0.949 mol) and dimethylformamide (0.25 ml, 3.16 mmol) was heated at reflux for 3 hours, cooled, and added gradually to a vigorously stirred mixture of ice and water (1.2 l) over 15 minutes. The resulting precipitate was filtered off and dried under reduced pressure at 80° C. to afford 2,3-dichloro-6,7-dimethyl-5-nitroquinoxaline (8.34 g, 97%), as a pale orange solid, mp 133°–134° C.

$^1$H NMR (300 MHz, DMSO-d$_6$): δ=2.38 (3H, s), 2.54 (3H, s), 8.12 (1H, s). v$_{max.}$ (KBr) 1537, 1388, 1377, 1269, 1163 cm$^{-1}$. m/z (thermospray) 289 (MNH$_4^+$).

(c) A mixture of 2,3-dichloro-6,7-dimethyl-5-nitroquinoxaline, 8.33 g, 30.6 mmol) and stannous chloride dihydrate (34.54 g, 153 mmol) in ethyl acetate (300 ml) was heated at reflux for 11 hours. A further portion of stannous chloride dihydrate (13.82 g, 61.2 mmol) was added and the mixture was heated for 2 hours, cooled and diluted with ethyl acetate (500 ml). The mixture was added to saturated aqueous sodium bicarbonate (200 ml) and filtered, washing the filter cake well with ethyl acetate. The organic layer was separated, washed with saturated aqueous sodium bicarbonate (3×100 ml), dried (MgSO$_4$) and concentrated under reduced pressure. The residue was purified by flash chromatography (gradient elution with methanol/dichloromethane) to afford 5-amino-2,3-dichloro-6,7-dimethylquinoxaline (6.15 g, 83%), as an orange solid, mp 178°–180° C.

$^1$H NMR (300 MHz, DMSO-d$_6$): δ=2.38 (3H, s), 2.54 (3H, s), 8.12 (1H, s). v$_{max}$ (KBr) 3475, 1613, 1267, 1178 cm$^{-1}$. m/z (thermospray) 242 (MNH$_4^+$).

(d) Sodium methoxide (25% solution in methanol, 13.9 ml, 61 mmol) was added over 12 minutes to a stirred solution of 5-amino-2,3-dichloro-6,7-dimethylquinoxaline (6.15 g, 25.4 mmol) in dry tetrahydrofuran (250 ml) under nitrogen at 0° C. The mixture was stirred at 0° C. for 20 minutes, and at room temperature for 72 hours. The mixture was diluted with ethyl acetate (750 ml), washed with water (2×250 ml) and brine (250 ml), dried (MgSO$_4$), and concentrated under reduced pressure. The residue was purified by flash chromatography (gradient elution with hexane/dichloromethane) to give 5-amino-2,3-dimethoxy-6,7-dimethylquinoxaline (4.55 g, 77%) as a white solid, mp 166°–167° C.

$^1$H NMR (300 MHz, CDCl$_3$): δ=2.32 (3H, s), 2.35 (3H, s), 4.14 (3H, s), 4.15 (3H, s), 5.06 (2H, broad s), 7.06 (1H, s). v$^{max.}$ (KBr) 3540, 2950, 1600, 1535, 1395, 1335, 1240 cm$^{-1}$. m/z (thermospray) 234 (MH$^+$).

(e) A mixture of 5-amino-2,3-dimethoxy-6,7-dimethylquinoxaline (50 mg, 0.214 mmol), methanesulphonic anhydride (187 mg, 1.07 mmol) and pyridine (87 ml, 1.07 mmol) in dry tetrahydrofuran (1 ml) was stirred at 20° C. for 2.7 hours. Water (0.3 ml) was added, and the mixture was stirred for 40 minutes. The mixture was partitioned between ethyl acetate (15 ml) and 2M hydrochloric acid (5 ml). The organic solution was washed with saturated aqueous sodium bicarbonate (5 ml), dried (MgSO$_4$), and concentrated under reduced pressure to give N-(2,3-dimethoxy- 6,7-dimethylquinoxalin-5-yl)methanesulphonamide (63 mg, 94%) as a white solid, mp 219° C.

$^1$H NMR (300 MHz, CDCl$_3$): δ=2.46 (3H, s), 2.55 (3H, s), 2.87 (3H, s), 4.16 (6H, s), 7.00 (1H, broad s), 7.57 (1H, s). ν$_{max.}$ (KBr) 3545, 1480, 1160 cm$^{-1}$. m/z (thermospray) 312 (MH$^+$).

Analysis %: Found C, 50.02; H, 5.48; N, 13.35; S, 10.51. C$_{13}$H$_{17}$N$_3$SO$_4$ requires C, 50.15; H, 5.50; N, 13.50; S, 10.30.

(f) N-(2,3-dimethoxy-6,7-dimethylquinoxalin-5-yl)-N-(methoxycarbonyl-methyl)methanesulphonamide was prepared from N-(2,3-dimethoxy-6,7-dimethylquinoxalin-5-yl) methanesulphonamide (1.00 g, 3.2 mmol) by the method of Example 3 step (g) and was obtained as a pale yellow solid (633 mg, 51%).

$^1$H NMR (300 MHz, CDCl$_3$) δ=2.45 (3H, s), 2.65 (3H, s), 3.15 (3H, s), 3.72 (3H, s), 4.13 (3H, s), 4.15 (3H, s), 4.44 (1H, d, J 18 Hz), 4.80 (1H, d, J 18 Hz), 7.64 (1H, s). m/z (thermospray) 384 (MH$^+$).

(g) The title compound was prepared from N-(2,3-dimethoxy-6,7-dimethylquinoxalin-5-yl)-N-(methoxycarbonylmethyl)methanesulphonamide (360 mg, 0.892 mmol) by the method of Example 1 step (i) and was obtained as a white solid (504 mg, 94%) mp>300° C.

Analysis %: Found, C, 45.31; H, 4.37; N, 12.13. C$_{13}$H$_{15}$N$_3$O$_6$S. 0.25H$_2$O requires: C, 45.15; H, 4.52; N, 12.15.

EXAMPLE 8

N-(Carboxymethyl)-N-(1,4-dihydro-6-chloro-7-ethyl-2,3-dioxoquinoxalin-5-yl) methanesulphonamide

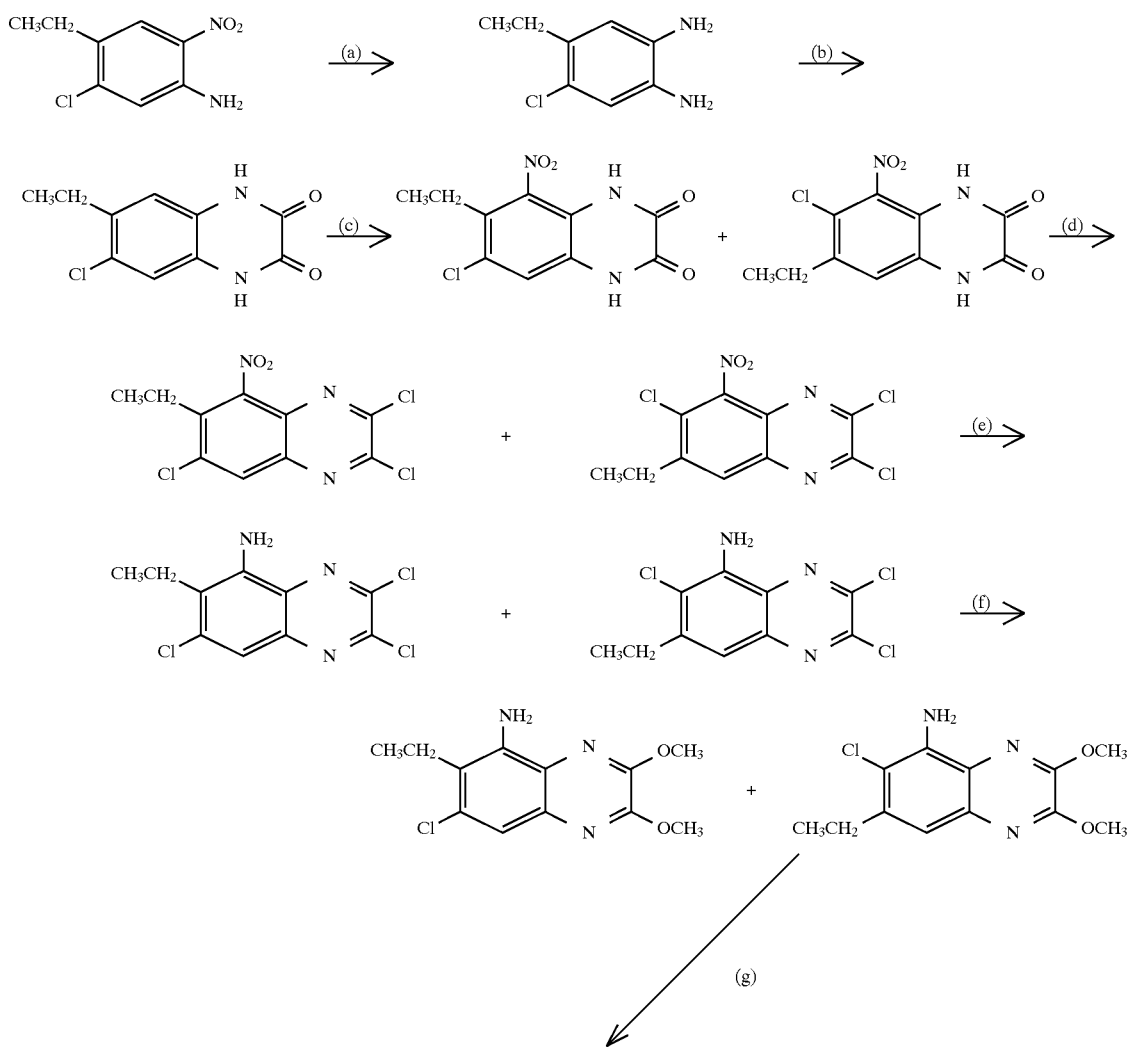

 (h)→ 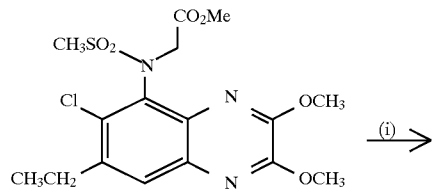 (i)→

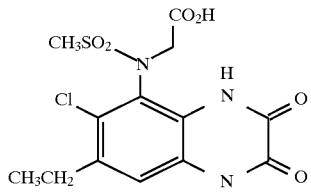

(a) A mixture of 5-chloro-4-ethyl-2-nitroaniline (supplied by the Sigma-Aldrich Library of Rare Chemicals, 2.62 g, 13.1 mmol), tin (II) chloride dihydrate (14.7 g, 65.3 mmol) and ethyl acetate (130 ml) was heated under reflux for 22h. The mixture was cooled and partitioned between 1M aqueous sodium hydroxide (500 ml) and ethyl acetate (500 ml). The aqueous layer was extracted with ethyl acetate (250 ml), and the combined organic solutions were washed with saturated aqueous sodium chloride (100 ml), dried (MgSO$_4$) and concentrated under reduced pressure to give 1,2-diamino4-chloro-5-ethylbenzene (2.70 g, >100%) as a white solid which was used directly without further purification.

$^1$H NMR (300 MHz, CDCl$_3$) δ=1.19 (3H, t, J 7 Hz), 2.63 (2H, q, J 7 Hz), 3.30 (4H, broad s), 6.57 (1H, s), 6.70 (1H, s).

(b) A mixture of 1,2-diamino4-chloro-5-ethylbenzene (2.70 g, ca 13 mmol), oxalic acid (1.65 g, 18.3 mmol) and 4M hydrochloric acid (66 ml) was heated at reflux for 4.6 h, cooled, and the grey solid collected by filtration and washed with water. The solid was dried under reduced pressure at 50° C. to afford 1,4-dihydro-6-chloro-7-ethylquinoxalin-2,3-dione (2.34 g, 80%), mp>315° C.

Analysis %: Found, C, 53.60; H, 3.87; N, 12.40. C$_{10}$H$_9$ClN$_2$O$_2$ requires: C, 53.47; H, 4.04; N, 12.47.

$^1$H NMR (300 MHz, DMSO-d$_6$) δ=1.17 (3H, t, J 7 Hz), 2.66 (2H, q, J 7 Hz), 7.05 (1H, s), 7.14 (1H, s), 11.78 (1H, broad s), 11.82 (1H, broad s).

(c) 1,4-Dihydro-6-chloro-7-ethylquinoxalin-2,3-dione (2.34 g, 10.4 mmol) was added in small portions over 10 minutes to vigorously stirred concentrated nitric acid (20 ml) at room temperature. The mixture was then heated at 40° C. for 12h, cooled, and poured into ice water. The yellow solid which formed was filtered off, washed with water, and dried to give 1,4-dihydro-6-chloro-7-ethyl-5-nitroquinoxalin-2,3-dione and 1,4-dihydro-7-chloro-6-ethyl-5-nitroquinoxalin-2,3-dione (2.55 g, 91%), as a mixture (1.7:1 ratio).

$^1$H NMR (300 MHz, DMSO-d$_6$) δ=1.09–1.19 (3H, m), 2.56 (1.3H, q, J 7 Hz), 2.71 (0.7H, q, J 7 Hz), 7.19 (0.4H, s), 7.29 (0.6H, s), 11.95–12.15 (2H, broad m). m/z (thermospray) 287 (MNH$_4^+$).

(d) A mixture of 1,4-dihydro-6-chloro-7-ethyl-5-nitroquinoxalin-2,3-dione and 1,4-dihydro-7-chloro-6-ethyl-5-nitroquinoxalin-2,3-dione (2.75 g, 11 mmol), thionyl chloride (28.6 ml, 0.305 mol) and N,N-dimethylformamide (85 μl, 1.0 mmol) was heated under nitrogen at reflux for 24h. The solution was cooled and cautiously added dropwise to stirred ice-water (600 ml). After 1 h, the beige solid was filtered off, washed with water and dried under reduced pressure to afford a mixture of 2,3,7-trichloro-6-ethyl-5-nitroquinoxaline and 2,3,6-trichloro-7-ethyl-5-nitroquinoxaline (2.26 g, 67%). Purification of the mixture by flash chromatography (eluting with hexane:dichloromethane 3:1) permitted isolation of small quantities of the two isomers for characterisation purposes. The first eluted isomer, 2,3,6-trichloro-7-ethyl-5-nitroquinoxaline had mp 106°–109° C.

Analysis %: Found C, 39.21; H, 1.99; N, 13.71. C$_{10}$H$_6$Cl$_3$N$_3$O$_2$ requires C, 39.18; H, 1.97; N, 13.71.

$^1$H NMR (300 MHz, CDCl$_3$) δ=1.41 (3H, t, J 7 Hz), 3.06 (2H, q, J 7 Hz), 8.02 (1H, s). m/z (thermospray) 323 (MH$^+$). The second eluted isomer, 2,3,7-trichloro-6-ethyl-5-nitroquinoxaline had mp 88°–92° C.

Analysis %: Found C, 39.06; H, 1.87; N, 13.85. C$_{10}$H$_6$Cl$_3$N$_3$O$_2$ requires C, 39.18; H, 1.97; N, 13.71.

$^1$H NMR (300 MHz, CDCl$_3$) δ=1.35 (3H, t, J 8 Hz), 2.98 (2H, q, J 8 Hz), 8.19 (1H, s). m/z (thermospray) 323 (MH$^+$).

(e) A mixture of 2,3,7-trichloro-6-ethyl-5-nitroquinoxaline and 2,3,6-trichloro-7-ethyl-5-nitroquinoxaline (200 mg, 0.652 mmol), tin (II) chloride dihydrate (1.03 g, 4.57 mmol) and ethyl acetate (6.5 ml) was heated under reflux for 4h, cooled and diluted with ethyl acetate. The solution was washed with 10% aqueous sodium carbonate (25 ml). The aqueous layer was extracted with ethyl acetate (2×25 ml), and the combined organic solutions were washed with 10% aqueous sodium carbonate (2×25 ml), saturated aqueous sodium chloride (25 ml), dried (MgSO$_4$) and concentrated under reduced pressure to give 5-amino-2,3,7-trichloro-6-ethylquinoxaline and 5-amino-2,3,6-trichloro-7-ethylquinoxaline as an orange solid (174 mg, 91%), ratio 1:1.

$^1$H NMR (300 MHz, CDCl$_3$) δ=1.25 (1.5H, t, J 8 Hz), 1.37 (1.5H, t, J 8 Hz), 2.84–2.98 (2H, m), 5.05 (1 H, broad s), 5.28 (1H, broad s), 7.22 (0.5H, s), 7.43 (0.5H, s).

(f) A mixture of 5-amino-2,3,7-trichloro6-ethylquinoxaline and 5-amino-2,3,6-trichloro-7-ethylquinoxaline (169 mg, 0.611 mmol) in anhydrous tetrahydrofuran (6 ml) was treated with a 25% solution of sodium methoxide in methanol (0.84 ml, 1.47 mmol) at 0° C. with stirring. After 3.5 hours, the solution was diluted with ethyl acetate, washed with water (2×10 ml), saturated aqueous sodium chloride (10 ml), dried (MgSO$_4$) and concentrated under reduced pressure. Purification by flash chromatography (eluting with hexane/ethyl acetate 19:1) gave two products. The first eluted compound, 5-amino-6-chloro- 7-ethyl-2,3-dimethoxyquinoxaline (42 mg, 26%), was obtained as a white solid.

¹H NMR (300 MHz, CDCl₃) δ=1.32 (3H, t, J 8 Hz), 2.87 (2H, q, J 7 Hz), 4.18 (6H, s), 4.90 (2H, br s), 7.08 (1H, s). The second eluted compound, 5-amino-7-chloro-6-ethyl-2,3-dimethoxy-quinoxaline (57 mg, 35%), was obtained as a pale green solid.

¹H NMR (300 MHz, CDCl₃) δ=1.14 (3H, t, J 7 Hz), 2.84 (2H, q, J 7 Hz), 4.12 (3H, s), 4.14 (3H, s), 4.70 (2H, broad s), 7.22 (1 H, s).

(g) Methanesulphonic anhydride (671 mg, 3.85 mmol) was added to a stirred solution of 5-amino-6-chloro-7-ethyl-2,3-dimethoxyquinoxaline (207 mg, 0.77 mmol) and anhydrous pyridine (305 mg, 3.85 mmol) in anhydrous tetrahydrofuran (7.7 ml) at room temperature. After 72h, water (3 ml) was added and the mixture was stirred for a further 60 minutes. The mixture was diluted with ethyl acetate and washed with 2M hydrochloric acid (50 ml), water (50 ml), saturated aqueous sodium bicarbonate (50 ml) and saturated aqueous sodium chloride (50 ml). The organic phase was dried (MgSO₄) and concentrated under reduced pressure to give N-(6-chloro-7-ethyl-2,3-dimethoxyquinoxalin-5-yl)methanesulphonamide (206 mg, 77%).

¹H NMR (300 MHz, CDCl₃) δ=1.37 (3H, t, J 8 Hz), 2.89–3.00 (2H, m), 3.39 (3H, s), 4.16 (3H, s), 4.19 (3H, s), 7.01 (1H, s), 7.60 (1H, s). m/z (thermospray) 346 (MH⁺).

(h) N-(6-Chloro-2,3-dimethoxy-7-ethylquinoxalin-5-yl)-N-(methoxycarbonyl-methyl)methanesulphonamide was prepared from N-(6-chloro-7-ethyl-2,3-dimethoxyquinoxalin-5-yl)methanesulphonamide (500 mg, 1.45 mmol) by the method of Example 3 step (g) but purifying the crude product by triturating with hexane instead of by flash chromatography.

The product was obtained as a white solid (455 mg, 75%), mp 160.5°–162.5° C.

Analysis %: Found C, 45.95; H, 4.78; N, 9.92. C₁₆H₂₀N₃O₆SCl requires C, 45.99; H, 4.82; N, 10.06.

(i) The title compound was prepared from N-(6-chloro-7-ethyl-2,3-dimethoxyquinoxalin-5-yl)-N-(methoxycarbonylmethyl)methanesulphonamide (300 mg, 0.719 mmol) by the method of Example 1 step (i) but after concentration under reduced pressure the crude product was dissolved in 1N sodium hydroxide, washed twice with dichloromethane and acidified with 2M hydrochloric acid. The resulting precipitate was collected by filtration and dried under reduced pressure to afford the title compound as a pale yellow solid (211 mg, 78%), mp 273°–275° C.

Analysis %: Found C, 40.27; H, 3.81; N, 10.74. C₁₃H₁₄N₃O₆SCl. 0.75H₂O requires C, 40.11; H, 4.01; N, 10.79.

EXAMPLE 9

N-(Carboxymethyl)-N-(1,4-dihydro-7-chloro-6-ethyl-2,3-dioxoquinoxalin-5-yl)methanesulphonamide

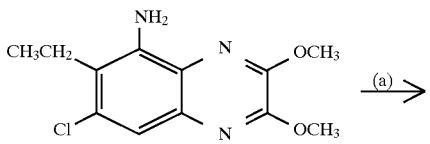

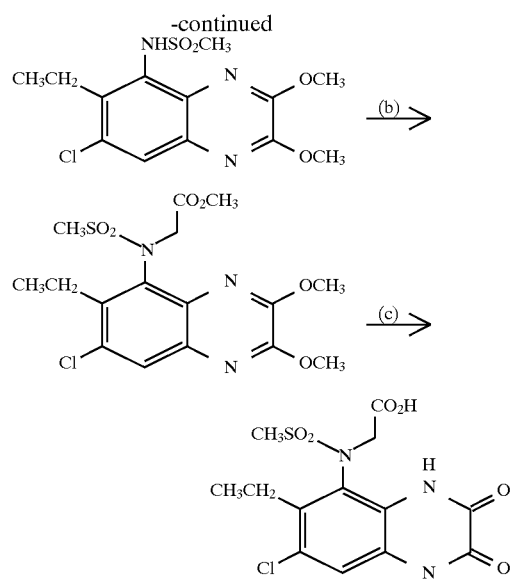

(a) 5-Amino-7-chloro-6-ethyl-2,3-dimethoxyquinoxaline (Example 8 step (f)) was converted to N-(7-chloro-6-ethyl-2,3-dimethoxyquinoxalin-5-yl)methanesulphonamide by the method of Example 8 step (g) and was obtained in 47% yield.

¹H NMR (300 MHz, CDCl₃) δ=1.25 (3H, t, J 8 Hz), 3.00 (3H, s), 3.28 (2H, q, J 7 Hz), 4.17 (3H, s), 4.27 (3H, s), 6.87 (1H, s), 7.83 (1H, s). m/z (thermospray) 346 (MH⁺).

(b) N-(7-Chloro-6-ethyl-2,3-dimethoxyquinoxalin-5-yl)-N-(methoxycarbonylmethyl)-methanesulphonamide was prepared from N-(7-chloro-6-ethyl-2,3-dimethoxyquinoxalin-5-yl)methanesulphonamide (500 mg, 1.45 mmol) by the method of Example 8 step (h) and was obtained as a white solid (497 mg, 82%), mp 165°–168° C.

Analysis %: Found C, 45.89; H, 4.81; N, 9.86. C₁₆H₂₀N₃O₆SCl requires C, 45.99; H, 4.82; N, 10.06.

(c) The title compound was prepared from N-(7-chloro-6-ethyl-2,3-dimethoxy-quinoxalin-5-yl)-N-(methoxycarbonylmethyl)methanesulphonamide (300 mg, 0.719 mmol) by the method of Example 8 step (i) and was obtained as a white solid (231 mg, 86%), mp>300° C. (decomposes).

Analysis %: Found C, 41.26; H, 3.67; N, 10.93. C₁₃H₁₄N₃O₆SCl requires C, 41.55; H, 3.76; N, 11.18.

EXAMPLE 10

N-(1,4-Dihydro-6-chloro-7-ethyl-2,3-dioxoquinoxalin-5-yl)-N-(methoxycarbonylmethyl)methanesulphonamide

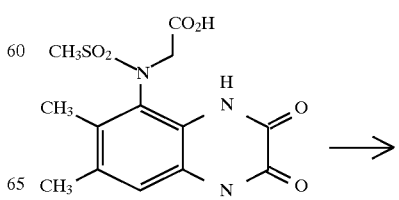

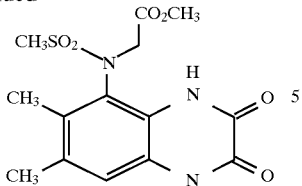

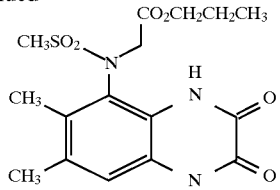

A mixture of N-(carboxymethyl)-N-(1,4-dihydro-6,7-dimethyl-2,3-dioxoquinoxalin-5-yl)methanesulphonamide (Example 7, 200 mg, 0.587 mmol) and methanol (10 ml) saturated with hydrogen chloride gas was heated at reflux for 18 hours and then allowed to cool to room temperature. The mixture was concentrated under reduced pressure and the residue triturated with methanol and dried under reduced pressure to give the title compound (122 mg, 59%) as a white solid, mp 296.5°–299° C.

Analysis %: Found C, 47.02; H, 4.77; N, 11.76. $C_{14}H_{17}N_3O_6S$ requires C, 47.32; H, 4.82; N, 11.82.

EXAMPLE 11

N-(1,4-Dihydro-6-chloro-7-ethyl-2,3-dioxoquinoxalin-5-yl)-N-(ethoxycarbonylmethyl)methanesulphonamide

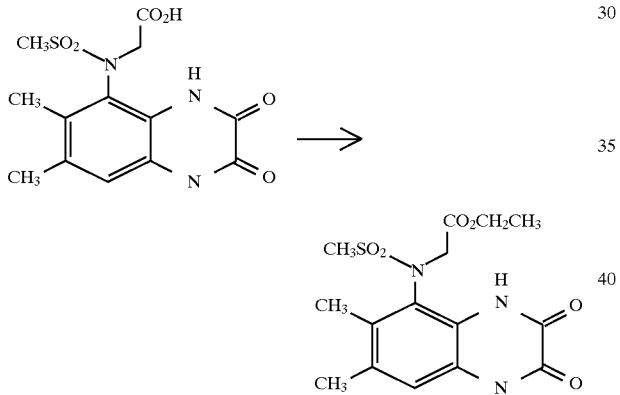

The title compound was prepared by the method of Example 10 substituting ethanol for methanol and was obtained as a white solid (87%), mp>300° C.

Analysis %: Found C, 48.41; H, 5.14; N, 11.35. $C_{15}H_{19}N_3O_6S$. $0.1H_2O$ requires C, 48.54; H, 5.21; N, 11.32.

EXAMPLE 12

N-(1,4-Dihydro-6-chloro-7-ethyl-2,3-dioxoquinoxalin-5-yl)-N-(n-proyloxycarbonylmethyl)methanesulphonamide

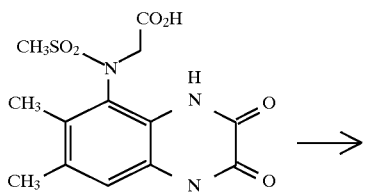

The title compound was prepared by the method of Example 10 substituting n-propanol for methanol and was obtained as a white solid (86%), mp 240°–242° C.

Analysis %: Found C, 49.93; H, 5.49; N. 10.87. $C_{16}H_{21}N_3O_6S$. $0.1H_2O$ requires C, 50.12; H, 5.52; N, 10.96.

EXAMPLE 13

(RS),(RS)-N-(1-Carboxyethyl)-N-(1,4-dihydro-6-chloro-7-methyl-2,3-dioxoquinoxalin-5-yl)methanesulphonamide

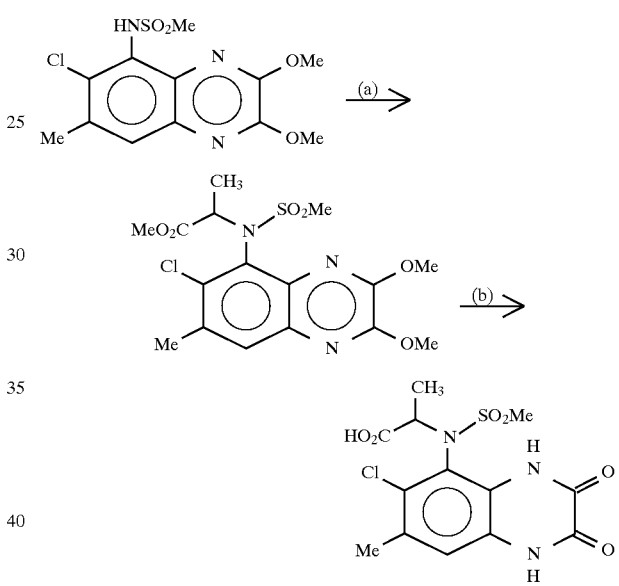

(a) (RS),(RS)-N-(6-chloro-7-methyl-2,3-dimethoxyquinoxalin-5-yl)-N-(1-methoxycarbonylethyl)methanesulphonamide was prepared from N-(6-chloro-2,3-dimethoxy-7-methylquinoxalin-5-yl)methanesulphonamide (Example 5, step (a)) by the method of Example 3 step (g), substituting methyl 2-bromopropionate for methyl bromoacetate, and obtained as a mixture of diastereoisomers (as determined by NMR) (48%). mp 142°–145° C.

$^1$H NMR (300 MHz, $CDCl_3$): δ=1.12 (2H,d, major, J 9 Hz), 1.27 (1H,d, minor, J 9 Hz), 2.58 (2H, s, major), 2.59 (1H, s. minor), 3.32 (2H, s, major), 3.36 (1H, s, minor), 3.63 (1H, s, minor), 3.82 (2H, s, major), 4.15 (2H, s, major), 4.17 (s, 1H, minor), 4.20 (2H, s, major), 4.22 (1 H, s, minor), 5.00 (1/3H, q, minor, J 9 Hz), 5.09 (2/3H, q, major J 9 Hz), 7.70 (2/3H, s, major), 7.72 (1/3H, s, minor). m/z (thermospray) 418 (MH$^+$).

(b) The title compound was prepared from the compound of step (a) (100 mg, 0.24 mmol) by the method of Example 1 step (i), but refluxing for 72 hours. The product was obtained as white solid (62 mg, 69%).

$^1$H NMR (300 MHz, DMSO-$d_6$): δ=1.81 (3H,d,J 8 Hz), 2.35 (3H,s), 3.13 (3H,s), 4.47 (1H,q,J 8 Hz), 7.14 (1H,s), 11.88, broad s), 12.12 (1H,broad s).

EXAMPLE 14

N-(1,4-Dihydro-6,7-dichloro-2,3-dioxoquinoxalin-5-yl)-N-( 1,3,4-oxadiazolon-5-yl)methyl methanesulphonamide

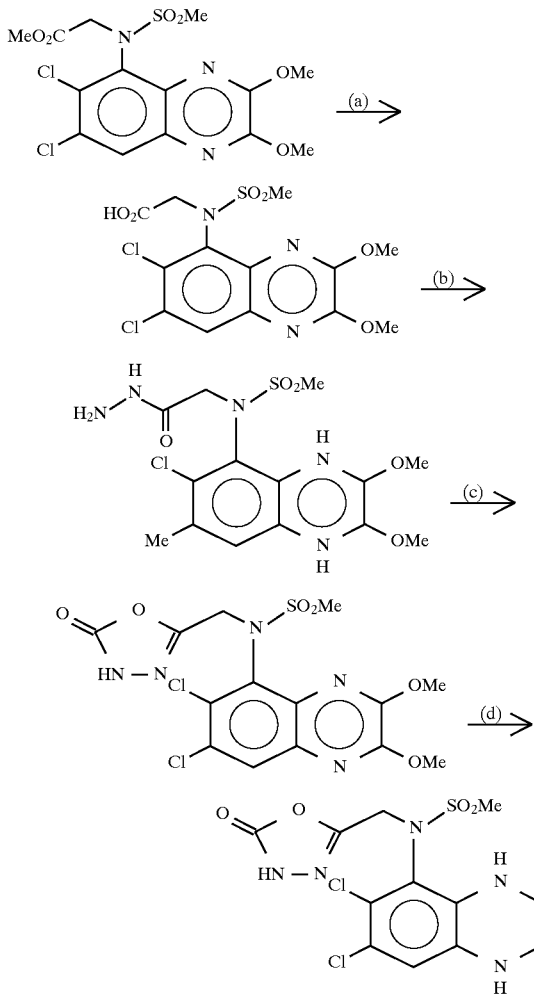

(a) A mixture of N-(6,7-dichloro-2,3-dimethoxyquinoxalin-5-yl)-N-(methoxycarbonylmethyl)-methanesulphonamide (Example 71, WO 96/09295, 1.0 g, 2.357 mmol), 1M sodium hydroxide (12 ml) and 1,4-dioxan (25 ml) was stirred at room temperature for 15 minutes. The resulting solution was acidified to ca. pH5 with 2M hydrochloric acid and concentrated under reduced pressure. The residue was suspended in water (10 ml), collected by filtration and dried under reduced pressure at 80° C. to give N-(carboxymethyl)-N-(6,7-dichloro-2,3-dimethoxyquinoxalin-5-yl)methanesulphonamide (876 mg, 91 %) as a white solid, mp 203°–206° C.

Analysis %: Found, C, 36.64; H, 3.12; N, 9.79. $C_{13}H_{13}Cl_2N_3O_6S$. 0.67 $H_2O$ requires C, 36.99; H, 3.42; N, 9.95.

(b) A mixture of N-(carboxymethyl)-N-(6,7-dichloro-2,3-dimethoxyquinoxalin-5-yl)methanesulphonamide (500 mg, 1.219 mmol) and N,N'-carbonyldiimidazole (296 mg, 1.828 mmol) in dry tetrahydrofuran (15 ml) was heated at reflux for 1 hour, cooled and concentrated under reduced pressure. The residue was partitioned between dichloromethane (20 ml) and water (10 ml). The organic solution was dried ($MgSO_4$) and concentrated under reduced pressure. The residue was dissolved in dry tetrahydrofuran and hydrazine hydrate (122 mg, 2.438 mmol) added. After stirring at room temperature for 3 hours, the solvent was removed under reduced pressure and the residue partitioned between dichloromethane (20 ml) and saturated brine (10 ml). The aqueous layer was extracted with dichloromethane (20 ml) and the combined organic solutions were dried ($MgSO_4$) and concentrated under reduced pressure. Purification by flash chromatography on silica gel, eluting with dichloromethane:methanol 98:2, gave N-(6,7-dichloro-2,3-dimethoxyquinoxalin-5-yl)-N-(hydrazinocarbonylmethyl)methanesulphonamide (150 mg, 29%) as a white solid.

$^1$H NMR (300 MHz, DMSO-$d_6$): δ=3.40 (3H,s), 4.07 (3H,s), 4.14 (3H,s), 4.15 (1H,d,J11 Hz), 4.62 (1H,d, J11 Hz), 8.06 (1H,s), 9.08 (1H, broad s). m/z (thermospray) 424 ($MH^+$).

(c) A mixture of the product of step (b) (150 mg, 0.354 mmol) and N,N'-carbonyidiimidazole (69 mg, 0.425 mmol) in 1,4-dioxan (4 ml) was heated at reflux for 3 hours, cooled to room temperature and concentrated under reduced pressure. The residue was purified by flash chromatography on silica gel, eluting with dichloromethane:methanol 98:2, to give N-(6,7-dichloro-2,3-dimethoxyquinoxalin-5-yl)-N-(1,3,4-oxadiazolon-5-yl)methanesulphonamide (89 mg, 56%) as a white solid.

Analysis %: Found, C, 37.19; H, 3.14; N, 14.52. $C_{14}H_{13}N_5O_6Cl_2S.0.19$ $CH_2Cl_2.0.05$ Dioxan requires: C,36.71; H, 2.95; N, 14.88. m/z (thermospray) 450 ($MH^+$).

(d) The title compound was prepared from the compound of step (c) (74 mg, 0.164 mmol) by the method of Example 1 step (i) and was obtained as a brown solid (48 mg, 69%).

$^1$H NMR (300 MHz, DMSO-$d_6$): δ=3.24 (3H,s), 4.18 (1H,d,J 18 Hz), 4.72 (1H, d,J 18 Hz), 7.40 (1H,s), 11.30 (1H broad s),12.24 (1H, broad s).

EXAMPLE 15

N-(1,4-Dihydro-6,7-dichloro-2,3-dioxoquinoxalin-5-yl)-N-(1,2,4-oxadiazolon-3-yl) methylmethanesulphonamide

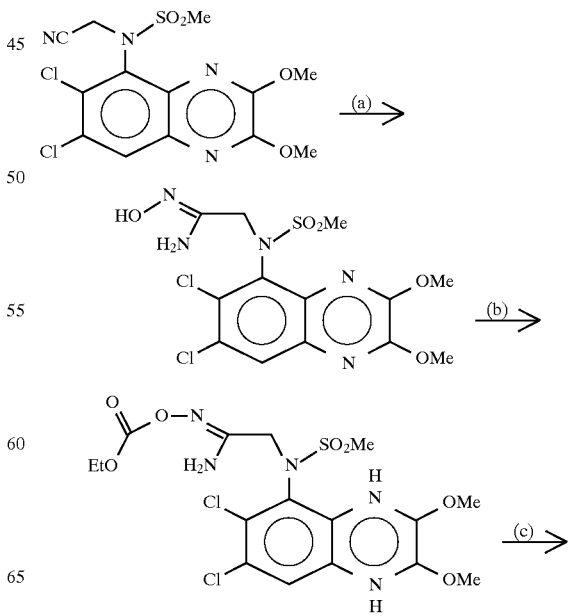

33
-continued

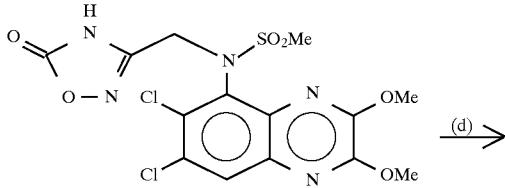

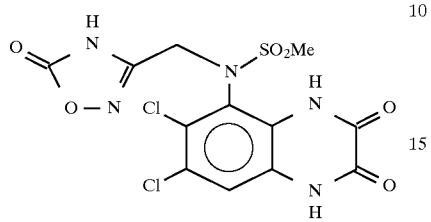

(a) A mixture of N-(6,7-dichloro-2,3-dimethoxyqunoxalin-5-yl)-N-(cyanomethyl)methanesulphonamide (Example 89(a), WO 96/09295, 1.54 g, 3.937 mmol), hydroxylamine hydrochloride (328 mg, 4.724 mmol) and sodium carbonate (250 mg, 2.362 mmol) in absolute ethanol (10 ml) was heated at reflux for 5 hours. The resulting suspension was filtered hot and the filtrate allowed to cool to room temperature. The precipitated crystals were collected by filtration and dried under reduced pressure at 60° C. to give N-(2-amino-2-hydroxyiminoethyl)-N-(6,7-dichloro-2,3-dimethoxyquinoxalin-5-yl)methanesulphonamide (852 mg, 51%).

$^1$H NMR (300 MHz, CDCl$_3$): δ=3.22 (3H,s), 4.15 (3H,s), 4.17 (3H,s), 4.29 (1H,d,J 12 Hz) 4.38 (1H,d, J12 Hz). 5.26 (2H, broad s), 7.96 (1H,s). m/z (thermospray) 424 (MH$^+$).

(b) The product of step (a) (852 g, 2.008 mmol) was dissolved in dry pyridine (12 ml) and cooled to 0° C. Ethyl chloroformate (479 mg, 4.418 mmol) was added over 5 minutes. The mixture was stirred at room temperature for 16 hours and poured into ice-cold water (40 ml). The resulting precipitate was collected by filtration and dried under reduced pressure at 60° C. to give N-(2-amino-2-ethoxycarbonyloxyiminoethyl)-N-(6,7-dichloro-2,3-dimethoxyquinoxalin-5-yl)methanesulphonamide (757 mg, 76%).

$^1$H NMR (300 MHz, CDCl$_3$) δ:1.30 (3H,t,J 8 Hz), 3.21 (3H,s), 4.14 (3H,s), 4.16 (3H,s), 4.20 (2H,q,J 8 Hz), 4.36 (1H,d,J 16 Hz), 4.50 (1H,d,J 16 Hz), 5.71 (2H, broad s), 7.97 (1 H,s). m/z (thermospray) 496 (MH$^+$).

(c) A mixture of the product of step (b) (387 mg, 0.78 mmol) and 1M sodium hydroxide (0.78 ml, 0.78 mmol) in tetrahydrofuran (4 ml) and water (4 ml) was stirred at room temperature for 2 hours, heated at 50° C. for 3 hours and then cooled to room temperature. The mixture was partitioned between ethyl acetate (20 ml) and 2M hydrochloric acid (20 ml). The aqueous layer was extracted with ethyl acetate (20 ml) and the combined organic solutions were dried (Na$_2$SO$_4$) and concentrated under reduced pressure. Purification by flash chromatography on silica gel, eluting with hexane:ethyl acetate 3:1 gave N-(6,7-dichloro-2,3-dimethoxyquinoxalin-5-yl)-N-(1,2,4-oxadiazolon-3-yl)methanesulphonamide as a white solid (137 mg, 39%).

$^1$H NMR (400 MHz, CDCl$_3$): δ=3.27 (3H,s), 4.18 (3H,s), 4.22 (3H,s), 4.62 (1H,d,J 14 Hz), 4.80 (1H,d, J14 Hz), 8.03 (1H,s). m/z (APCI) 450 (MH$^+$).

(d) The title compound was prepared from the product of step (c) (122 mg, 0.271 mmol) by the method of Example 1 step (i) and was obtained as an off-white solid (38 mg, 33%) mp>300° C.

34

Analysis %: Found, C, 32.30; H, 2.77; N, 15.13. C$_{12}$H$_9$N$_5$O$_6$Cl$_2$S. 1.6 H$_2$O requires: C, 31.96; H, 2.73; N, 15.53.

EXAMPLE 16

(RS).(RS)-N-(α-carboxybenzyl)-N-(1,4-dihydro-6-chloro-7-methyl-2,3-dioxoquinoxalin-5-yl)methanesulphonamide

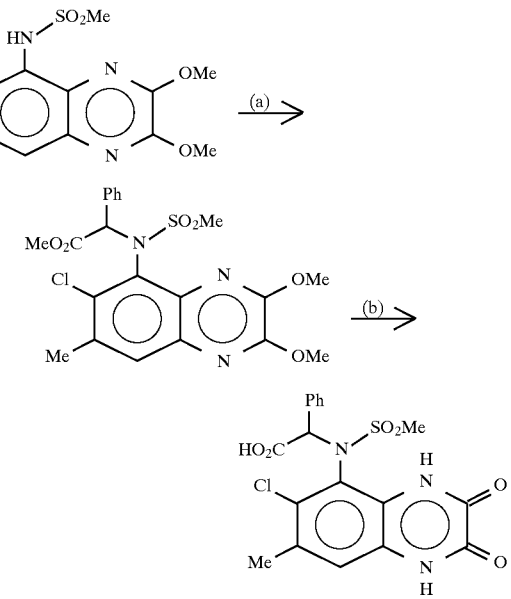

(a) (RS),(RS)-N-(6-chloro-7-methyl-2,3-dimethoxyquinoxalin-5-yl-N-(α-methoxycarbonylbenzyl)methanesulphonamide was prepared from N-(6-chloro-2,3-dimethoxy-7-methylquinoxalin-5-yl)methanesulphonamide (Example 5 step (a)) by the method of Example 3 step (g), substituting methyl-α-bromophenylacetate for methyl bromoacetate, and obtained as a mixture of diastereoisomers (as determined by NMR) (87%). mp 214°–217° C.

Analysis %: Found, C, 52.35; H, 4.61; N, 8.55. C$_{21}$H$_{22}$N$_3$O$_6$ClS requires: C, 52.56; H, 4.62; N, 8.76.

(b) The title compound was prepared from the product of step (a) (150 mg, 0.313 mmol) by the method of Example 1 step (i), but refluxing for 120 hours. The product was obtained as an off-white solid (89 mg, 65%). mp 279° C. (decomposes).

Analysis %: Found, C, 46.24; H, 4.25; N, 8.39. C$_{18}$H$_{16}$N$_3$O$_6$S. 2H$_2$O. 0.17 Et$_2$O requires: C, 46.12; H, 4.50; N, 8.64. m/z (thermospray) 455 (MNH$_4^+$).

EXAMPLE 17

N-(4-Carboxybutyl-N-(1,4-dihydro-6-chloro-7-methyl-2,3-dioxouinoxalin-5-yl)methanesulphonamide

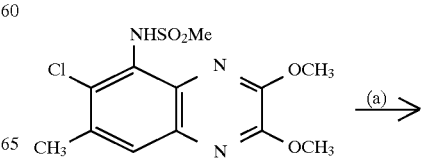

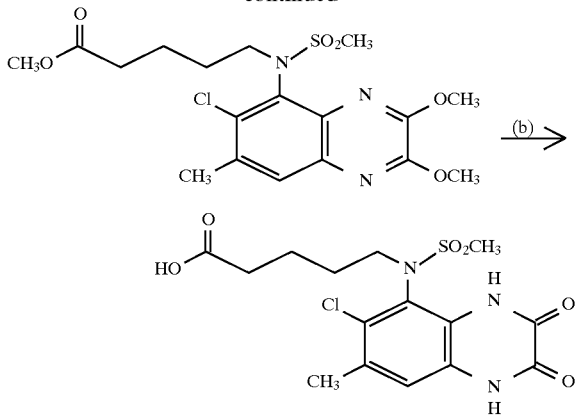

(a) N-(6-Chloro-7-methyl-2,3-dimethoxyquinoxalin-5-yl)-N-(4-methoxycarbonylbutyl)methanesulphonamide was prepared from N-(6-chloro-2,3-dimethoxy-7-methylquinoxalin-5-yl)methanesulphonamide (Example 5, step (a)) (1.00 g, 3.01 mmol) by the method of Example 3, step (g) substituting methyl-5-bromovalerate (1.16 g, 6.03 mmol) for methyl bromoacetate, and obtained as a white solid (0.77 g, 57%).

¹H NMR (300 MHz, CDCl₃): δ=1.57–1.70(4H, m), 2.24 (2H, t, J 6 Hz), 2.48 (3H, s), 3.19 (3H, s), 3.61 (3H, s), 3.80 (2H, t, J6 Hz), 4.17 (6H,s), 7.71 (1H,s). m/z (thermospray) 446 (MH⁺).

(b) The title compound was prepared from the product of step (a) (0.82 g, 1.85 mmol) by the method of Example 1, step (i) and was obtained as a beige solid (0.68 g, 91%).

Analysis %: Found, C, 44.32; H, 4.51; N, 10.18. C₁₅H₁₈ClN₃O₆S. requires C; 44.61 H, 4.49; N, 10.41. m.p. 244°–247° C.

EXAMPLE 18

N-(3-Carboxypropyl)-N-(1,4-dihydro-6-chloro-7-methyl-2,3-dioxoquinoxalin-5-yl)methanesulphonamide

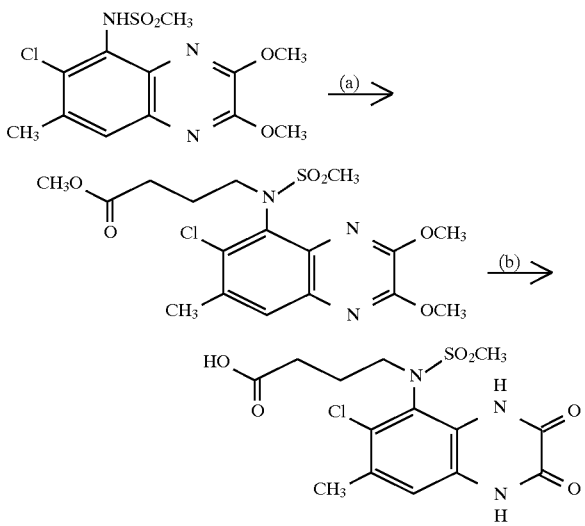

(a) N-(6-Chloro-7-methyl-2,3-dimethoxyquinoxalin-5-yl)-N-(3-methoxycarbonylpropyl)methanesulphonamide was prepared from N-(6-chloro-2,3-dimethoxy-7-methylquinoxalin-5-yl)methanesulphonamide (Example 5, step (a)) (250 mg, 0.75 mmol) by the method of Example 3, step (g), substituting methyl4-bromobutyrate (273 mg, 1.57 mmol) for methylbromoacetate, and obtained as a white solid (199 mg, 61%).

¹H NMR (300 MHz, CDCl₃): δ=1.85 (2H,m), 2.49 (2H,t, J6 Hz), 2.58 (3H,s), 3.20 (3H,s), 3.64 (3H,s), 4.88 (2H,m), 4.26 (3H,s), 4.28 (3H,s), 7.70 (1H,s). m/z (thermospray) 432 MH⁺.

(b) The title compound was prepared from N-(6-chloro-7-methyl-2,3-dimethoxy quinoxalin-5-yl)-N-(3-methoxycarbonylpropyl)methanesulphonamide (242 mg, 0.56 mmol) by the method of Example 1 step (i) and was obtained as a beige solid (171 mg, 78%).

Analysis %: Found, C,42.22; H,4.23; N,10.31. C₁₄H₁₆ClN₃O₆S.0.5 H₂O requires C,42.16; H,4.30; N,10.54. m.p. 285°–287° C.

EXAMPLE 19

N-(2-Carboxyethyl)-N-(1,4-dihydro-6-chloro-7-methyl-2,3-dioxoquinoxalin-5-yl)methanesulphonamide

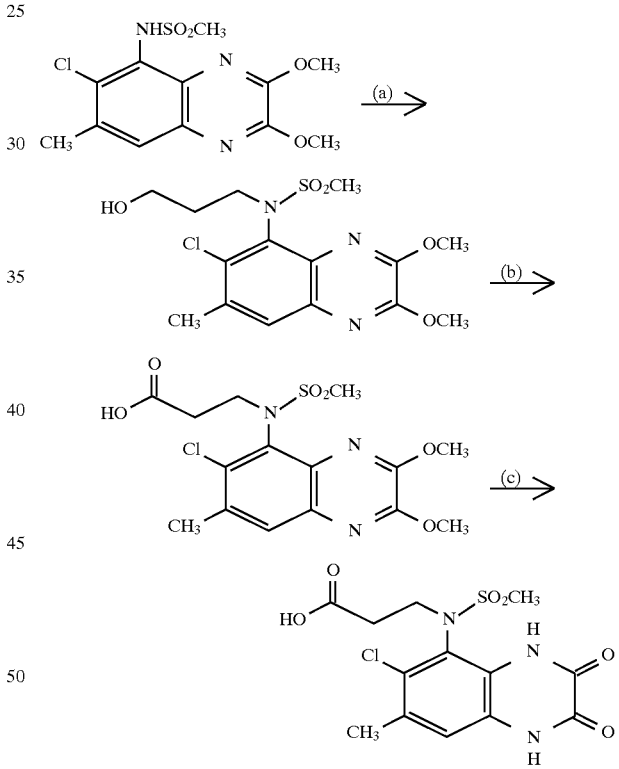

(a) N-(6-chloro-7-methyl-2,3-dimethoxyquinoxalin-5-yl)-N-(3-hydroxypropyl)methanesulphonamide was prepared from N-(6-chloro-2,3-dimethoxy-7-methylquinoxalin-5-yl)methanesulphonamide (Example 5, step (a)) (1.0 g, 3.01 mmol) by the method of Example 3, step (g) substituting 3-bromo-1-propanol (0.84 g, 6.03 mmol) for methylbromoacetate and obtained as a white solid (1.05 g, 89%).

¹H NMR (300 MHz, CDCl₃): 1.62–1.78 (2H,m), 2.58 (3H,s), 3.19 (3H,s), 3.78–4.10 (4H,m), 4.15 (3H,s), 4.18 (3H,s), 7.72 (1H,s). m/z (thermospray) 390 MH⁺.

(b) N-(6-Chloro-7-methyl-2,3-dimethoxyquinoxalin-5-yl)-N-(3-hydroxypropyl)methanesulphonamide (0.94 g, 2.41 mmol) and pyridinium dichromate (2.42 g, 9.63 mmol) in DMF (24 ml) were stirred at room temperature for 18 hours. The reaction mixture was poured into water (25 ml) and extracted twice with dichloromethane. The combined dichloromethane extracts were extracted twice with 10% potassium carbonate solution. The potassium carbonate extracts were acidified to pH1 with 2M HCl and extracted twice with dichloromethane. These combined dichloromethane extracts were dried (MgSO$_4$) and concentrated under reduced pressure to give N-(2-carboxyethyl)-N-(6-chloro-7-methyl-2,3-dimethoxyquinoxalin-5-yl) methanesulphonamide an off-white solid (0.49 g, 51%).

$^1$H NMR (300 MHz, CDCl$_3$): 2.57 (3H,s), 2.69 (2H,m), 3.22 (3H,s), 4.09 (2H, obs), 4,12 (3H,s), 4.16 (3H,s), 7.70 (1H,s). m/z (thermospray) 404 MH$^+$.

(c) The title compound was prepared from the product of step (b) (560 mg, 1.39 mmol) by the method of Example 1, step (i), and was obtained as an off-white solid (400 mg, 77%).

$^1$H NMR (300 MHz, DMSO-d$_6$): 2.31 (3H,s), 2.37–2.77 (2H, obscured m), 3.19 (3H,s), 3.71–3.83 (1H,m), 3.89–4.00 (1H,m), 7.07 (1H,s), 11.62 (1H,brs), 12.09 (1H,brs). m/z (thermospray) 393 MNH$_4^+$.

EXAMPLE 20

N-(1,4-Dihydro-6,7-dichloro-2,3-dioxoquinoxalin-5-yl)-N-(methanesulphonylamino-2-oxo-ethyl) methanesulphonamide

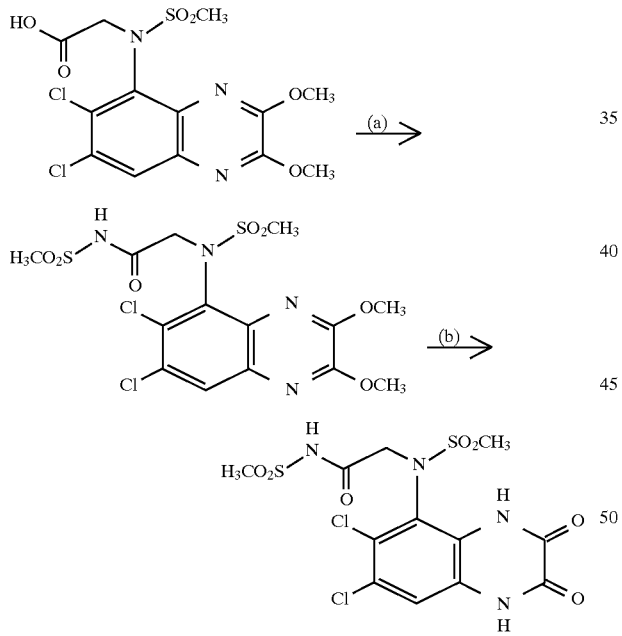

(a) DMF (8 mg, 0.11 mmol) was added dropwise to a suspension of N-(carboxymethyl)-N-(6,7-dichloro-2,3-dimethoxyquinoxalin-5-yl)methanesulphonamide (450 mg, 1.10 mmol, see Example 14, step (a)) and oxalyl chloride (209 mg, 1.65 mmol) causing an evolution of gas. After stirring at room temperature for 30 minutes all the solid had dissolved and the gas evolution had ceased giving a solution of the acid chloride (solution A).

Sodium hydride (53 mg, 2.19 mmol) was suspended in DMF at 0° C. under nitrogen. Methanesulphonamide (209 mg, 2.19 mmol) was added in two portions to the sodium hydride and a gas evolution occurred (solution B). The reaction mixture was stirred at 0° C. for 10 minutes. Solution A was added via cannula to solution B forming a brown solution which was stirred at room temperature for 18 hours. The reaction mixture was concentrated under reduced pressure and the brown residue dissolved in dichloromethane. The dichloromethane solution was washed with 2M hydrochloric acid, water and saturated brine and then dried (MgSO$_4$) and concentrated under reduced pressure. The residue was purified by flash chromatography on silica gel eluting with 95:5 dichloromethane:methanol to give N-(6,7-dichloro-2,3-dimethoxyquinoxalin-5-yl)-N-(methanesulphonylamino-2-oxo-ethyl) methanesulphonamide (174 mg, 33%).

$^1$H NMR (300 MHz, CDCl$_3$) δ: 3.19 (3H,s), 3.23 (3H,s), 4.18 (3H,s), 4.30 (3H,s), 4.51 (2H,q, J17 Hz), 8.01 (1H,s, obs). m/z (thermospray) 487 MH$^+$.

(b) The title compound was prepared from the product of step (a) (170 mg, 0.35 mmol) by the method of Example 1, step (i), but purifying the solid by flash chromatography on silica gel eluting with 9:1 dichloromethane:methanol to give an off-white solid (82 mg, 51%).

$^1$H NMR (300 MHz, DMSO-d$_6$): δ=2.78 (3H,s), 3.29 (3H,s), 3.63 (1H,d, J18 Hz), 4.26 (1H,d, J18 Hz), 7.26 (1H,s), 13.30 (1H,br,s). m/z (thermospray) 476 MNH$_4^+$.

EXAMPLE 21

N-(1,4-dihydro-6-chloro-7-methyl-2,3-dioxoquinoxalin-5-yl)-N-[3-(2-naphthyl)-3-carboxypropyl]methanesulphonamide

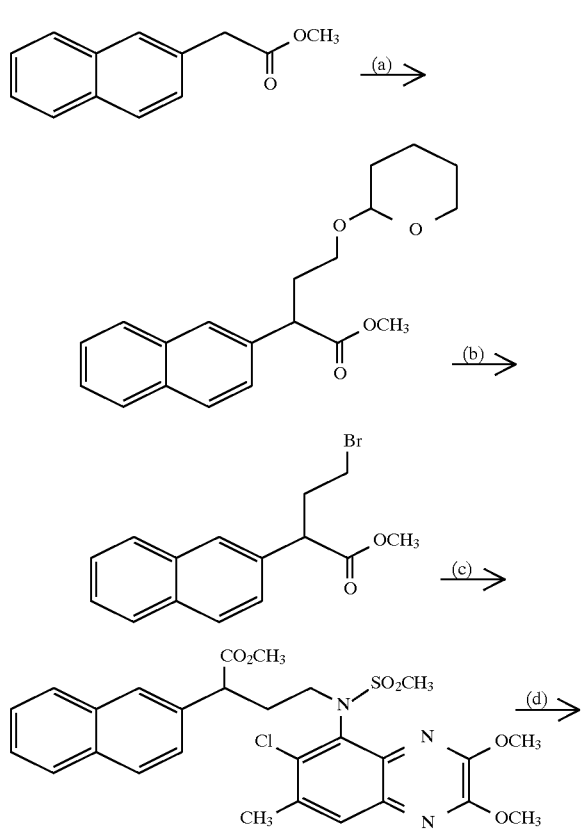

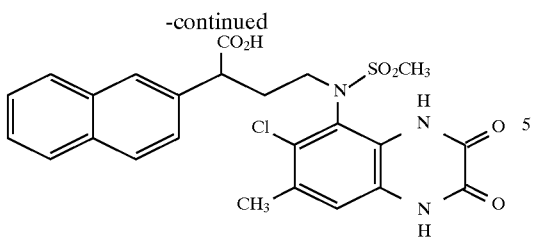

(a) Sodium hydride (0.28 9, 11.7 mmol) was suspended in DMF (20 ml) at 0° C. under nitrogen. 2-(Methoxycarbonylmethyl)naphthalene (J. Am. Chem. Soc., 1971, 93, 4919, 2.13 g, 10.6 mmol) dissolved in DMF (20 ml) was added dropwise to the suspension forming a deep yellow solution. The reaction mixture was stirred at 0° C. for 1 hour. 2-Bromo-1-(2'-tetrahydropyranylhydroxy)ethane (J. Med. Chem., 1975, 18, p992; 2.67 g, 12.8 mmol) dissolved in DMF (20 ml) was added dropwise to the reaction mixture and stirred for 18 hours. The reaction mixture was concentrated under reduced pressure. The solid was dissolved in dichloromethane and washed with water, saturated ammonium chloride solution, water and saturated brine and then dried ($MgSO_4$) and concentrated under reduced pressure. The resulting solid was purified by flash chromatography on silica gel eluting with 1:1 dichloromethane:hexane to give 2-[3-(2-naphthyl)-3-(methoxycarbonyl)propyloxy]tetrahydropyran as a pale yellow oil (2.00 g, 57%).

$^1$H NMR (300 MHz $CDCl_3$): δ=1.45–1.61 (2H,m, obs), 1.62–1.78 (1H,m), 1.78–1.92 (1H,m), 2.06–2.20 (1H,m), 2.42–2.59 (1H,m), 3.21–3.31 (1H,m), 3.32–3.52 (2H,m), 3.63 (3H,s), 3.70–3.90 (2H,m), 4.93–4.01 (1H,m), 4.46 (1H, brs), 4.52 (1H, brs), 7.20–7.50 (3H,m), 7.70–7.83 (4H,m). m/z (thermospray) 346 $MNH_4^+$.

(b) The product of step (a) (2.0 g, 6.1 mmol) and carbon tetrabromide (2.83 g, 8.5 mmol) were dissolved in dichloromethane (30 ml) and cooled to 0° C. under nitrogen. Triphenylphosphine (4.48 g, 17.1 mmol) was added portionwise turning the reaction mixture deep yellow. After stirring at room temperature for 18 hours the reaction mixture was concentrated under reduced pressure. The oil was purified by flash chromatography on silica gel eluting with 1:1 dichloromethane:hexane to give 1-bromo-3-(methoxycarbonyl)-3-(2-naphthyl)propane as a white solid (0.56 g, 30%).

$^1$H NMR (300 MHz, $CDCl_3$): δ=2.58–2.68 (1H,m), 2.60–2.76 (1H,m), 3.18–3.26 (1H,m), 3.38–3.45 (1H,m), 3.66 (3H,s), 4.07 (1H,t, J8 Hz), 7.39–7.52 (3H,m), 7.77 (1H,s), 7.82 (3H,m).

(c) N-(6-Chloro-7-methyl-2,3-dimethoxyquinoxalin-5-yl)-N-[3-(2-naphthyl)-3-(methoxycarbonyl)propyl]methanesulphonamide was prepared from N-(6-chloro-2,3-dimethoxy-7-methylquinoxalin-5-yl)methanesulphonamide (Example 5, step (a)) (250 mg, 0.75 mmol) by the method of Example 3 step (g), but substituting 1-bromo-3-(methoxycarbonyl)-3-(2-naphthyl)propane (463 mg, 1.51 mmol) for methylbromoacetate, and obtained as a white foam (335 mg, 80%).

Analysis %: Found, C,57.39; H,5.02; N,7.43. $C_{27}H_{28}ClN_3O_6S.1/2\ H_2O$ requires C,57.19; H,5.15; N,7.41. m/z (thermospray) 558 $MH^+$.

(d) The title compound was prepared from the product of step (c) by the method of Example 1, step (i). The solid was purified by flash chromatography on silica gel eluting with 9:1 dichloromethane:methanol to give a pale pink solid (239 mg, 80%).

Analysis %: Found, C,52.44; H,4.47; N,7.57. $C_{24}H_{22}ClN_3O_6S.H_2O.1/4$ dichloromethane requires C,52.46, H,4.45; N,7.57. m.p. 215° C. (decomposes).

EXAMPLE 22

The binding affinity for the glycine site of the NMDA receptor of some of the compounds of the examples were determined in test (a) above, and those found to have an $IC_{50}$ of less than 100nM included the compounds of the following examples: 1, 2, 3, 4, 5 [the (−)-isomer], 7, 10, 11 and 12.

We claim:

1. A compound of formula I,

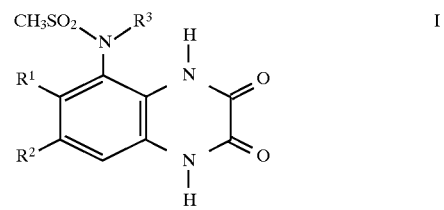

wherein $R^1$ and $R^2$ independently represent Cl or $C_{1-6}$ alkyl;

$R^3$ represents $XCO_2R^4$, $XCONHSO_2R^5$, $YNHSO_2R^5$ or $XR^6$;

$R^4$ represents H or $C_{1-6}$ alkyl optionally substituted by aryl or heterocyclyl;

$R^5$ represents $CF_3$, heterocyclyl or $C_{1-6}$ alkyl optionally substituted by aryl or heterocyclyl $R^6$ represents an acidic heterocycle;

X represents a $C_{1-6}$ alkyl diradical optionally substituted by aryl or heterocyclyl; and Y represents a $C_{2-6}$ alkyl diradical optionally substituted by aryl or heterocyclyl;

provided that when $R^1$ and $R^2$ each represent Cl or $C_{1-4}$, then $R^3$ does not represent $XCO_2H$, $CH_2CO_2CH_3$, $CH_2CH_2NHSO_2CF_3$ or 5-tetrazolylmethyl; and pharmaceutically acceptable salts thereof.

2. A compound as claimed in claim 1, wherein $R^1$ represents Cl.

3. A compound as claimed in claim 1, wherein $R^2$ represents methyl.

4. A compound as claimed in claim 1 wherein $R^3$ represents $CH_2CO_2H$, $CH(CH_3)CO_2H$, or $(CH_2)_3CO_2H$.

5. A pharmaceutical composition comprising a compound of formula I, as defined in claim 1, or a pharmaceutically acceptable salt thereof, in admixture with a pharmaceutically acceptable adjuvant, diluent or carrier.

6. An anxiolytic, anticonvulsant, analgesic or neuroprotective method of treatment, which comprises administration of a compound of formula I, as defined in claim 1, or a pharmaceutically acceptable salt thereof, to a patient in need of such treatment.

7. A process for the production of a compound of formula I, as defined in claim 1, or a pharmaceutically acceptable salt thereof, which comprises removing the protecting groups from a compound of formula II,

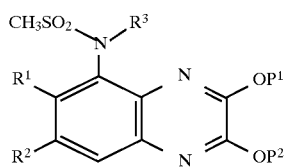
II
wherein $R^{1-3}$ are as defined in claim 1 and $P^1$ and $P^2$ are hydroxy protecting groups, and where desired or necessary converting the resulting compound into a pharmaceutically acceptable salt or vice versa.
8. A compound of formula II, as defined in claim 7.
* * * * *